(12) United States Patent
Sauve et al.

(10) Patent No.: US 11,098,076 B2
(45) Date of Patent: Aug. 24, 2021

(54) SYNTHESES, ACTIVITIES, AND METHODS OF USE OF DIHYDRONICOTINAMIDE RIBOSIDE DERIVATIVES

(71) Applicant: Cornell University, Ithaca, NY (US)

(72) Inventors: Anthony Sauve, New Rochelle, NY (US); Farheen Sultana Mohammed, Jackson Heights, NY (US); Yue Yang, New York, NY (US)

(73) Assignee: Cornell University, Ithaca, NY (US)

(*) Notice: Subject to any disclaimer, the term of this patent is extended or adjusted under 35 U.S.C. 154(b) by 0 days.

(21) Appl. No.: 16/551,401

(22) Filed: Aug. 26, 2019

(65) Prior Publication Data
US 2019/0382436 A1 Dec. 19, 2019

Related U.S. Application Data

(63) Continuation of application No. 15/744,602, filed as application No. PCT/US2016/042600 on Jul. 15, 2016, now Pat. No. 10,392,414.

(60) Provisional application No. 62/192,917, filed on Jul. 15, 2015.

(51) Int. Cl.
| | |
|---|---|
| *A61K 31/706* | (2006.01) |
| *C07H 19/048* | (2006.01) |
| *A23L 33/10* | (2016.01) |
| *C07H 1/00* | (2006.01) |
| *C07H 19/04* | (2006.01) |
| *C07H 1/06* | (2006.01) |

(52) U.S. Cl.
CPC ............ *C07H 19/048* (2013.01); *A23L 33/10* (2016.08); *A61K 31/706* (2013.01); *C07H 1/00* (2013.01); *C07H 1/06* (2013.01); *C07H 19/04* (2013.01); *A23V 2002/00* (2013.01)

(58) Field of Classification Search
None
See application file for complete search history.

(56) References Cited

U.S. PATENT DOCUMENTS

| | | | |
|---|---|---|---|
| 5,658,576 A | 8/1997 | Soudant | |
| 7,138,122 B2 * | 11/2006 | Burke | A61P 43/00 424/181.1 |
| 10,183,036 B2 * | 1/2019 | Dellinger | A61K 31/706 |
| 2007/0117765 A1 | 5/2007 | Sauve et al. | |
| 2009/0298808 A1 | 12/2009 | Yao et al. | |
| 2015/0072950 A1 | 3/2015 | Sauve et al. | |

FOREIGN PATENT DOCUMENTS

| | | |
|---|---|---|
| WO | WO 2011/133447 A1 | 10/2011 |
| WO | WO 2014/014828 A1 | 1/2014 |
| WO | WO 2015/014722 A1 | 2/2015 |
| WO | WO 2015/186114 A1 | 12/2015 |
| WO | WO 2016/149395 A1 | 9/2016 |

OTHER PUBLICATIONS

U.S. Appl. No. 15/744,602, filed Jan. 12, 2018.
Araki et al., "Increased Nuclear NAD Biosynthesis and SIRT1 Activation Prevent Axonal Degeneration", *Science*, 305:1010-1013 (2004).
Berge et al., Journal of Pharmaceutical Sciences, 66(1): 1-19 (1977).
Davies, Simple Synthesis of the 5-O-Benzoylriboside of 1,4-Dihydronicotinic Acid; a Cofactor for DT Diaphorase and Nitroreductase Enzymes, *Nucleosides, Nucleotides and Nucleic Acids*, 14(3-5): 311-312 (1995).
Friedlos et al., Identification of novel reduced pyridinium derivatives as synthetic co-factors for the enzyme DT diaphorase (NAD(p)H dehydrogenase (quinone), EC 1.6.99.2), *Biochemical Pharmacology*, 44(1): 25-31 (1992).
Knox et al., Virtual Cofactors for an *Escherichia coli* Nitroreductase Enzyme: Relevance to Reductively Activated Prodrugs in Antibody Directed Enzyme Prodrug Therapy (Adept), *Biochemical Pharmacology*, 49(11): 1641-1647 (1995).
Lopez-Lluch et al., "Mitochondrial biogenesis and healthy aging", *Experimental Gerontology*, Sep. 2009, 43 (9): 813-819 (2008).
Remington's Pharmaceutical Sciences, 18th ed., Mack Publishing Company, Easton, PA, 1990, p. 1445 (Table of Contents Only).
Tietze et al., Synthesis of 1,4-Dihydropyridine Nucleosides by Photochemical Cycloaddition, *Angewandte Chemie International Edition*, 24(2): 127-128 (1985).
Trissel, Handbook on Injectable Drugs, 4th ed., pp. 622-630 (1986).
Wang et al., "A local mechanism mediates NAD-dependent protection of axon degeneration," *J. Cell Biol.* 170(3): 349-355 (2005).
European Patent Office, extended European Search Report in Application No. 16825278.1 (dated Jun. 28, 2018).
WIPO, PCT International Search Report in Application No. PCT/US16/42600 dated Sep. 26, 2016, 3 pages.

* cited by examiner

*Primary Examiner* — Traviss C McIntosh, III
(74) *Attorney, Agent, or Firm* — Leydig, Voit & Mayer, Ltd.

(57) ABSTRACT

Disclosed is a compound of formula (I):

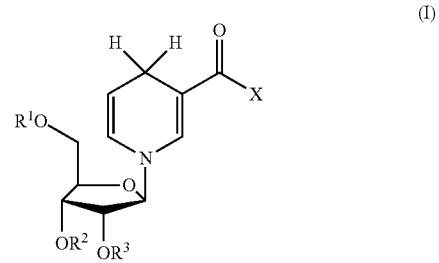

wherein $R^1$, $R^2$, $R^3$, and are as defined herein. Also disclosed are methods for increasing mammalian cell $NAD^+$ production and improving mitochondrial cell densities comprising administering to a cell the compound or a salt thereof.

13 Claims, 12 Drawing Sheets

SYNTHESES, ACTIVITIES, AND METHODS OF USE OF DIHYDRONICOTINAMIDE RIBOSIDE DERIVATIVES

CROSS-REFERENCE TO RELATED APPLICATIONS

This patent application is a Continuation of U.S. patent application Ser. No. 15/744,602, filed Jan. 12, 2018, which is the U.S. national stage of International Patent Application No. PCT/US2016/042600, filed Jul. 15, 2016, which claims the benefit of U.S. Provisional Patent Application No. 62/192,917, filed Jul. 15, 2015, the disclosures of which are incorporated in their entireties by reference for all purposes.

BACKGROUND OF THE INVENTION

Nicotinamide riboside and derivatives thereof, including nicotinate riboside, nicotinamide mononucleotide, and nicotinate mononucleotide, are metabolites of nicotinamide adenine dinucleotide ($NAD^+$). Current work available as state of the art establishes that increasing mammalian cell and tissue $NAD^+$ production can provide a number of health benefits, these include but are not limited to protection from neurodegeneration caused by Alzheimer's disease, resistance of mammals to toxic effects of high fat diets, improvement in mitochondrial densities in animals, improvement in insulin sensitivity and improved exercise endurance. Other work has provided hints at protection from neurotrauma, such as blast injury and noise induced hearing loss by enhancing $NAD^+$. Neurogenesis has also been linked to this effect. $NAD^+$ enhancement by pharmacologic agents mimics the effects of low calorie diets and exercise on physiology, and is a low toxicity method for mimicking the beneficial effects of these health beneficial regimes on human physiology. Moreover, the effect of increased physiologic $NAD^+$ appears to be to increased sirtuin activity, which is responsible for some of the beneficial effects observed for low calorie diets and exercise on human physiology.

While nicotinamide riboside and ester analogs thereof are useful as efficient precursors of $NAD^+$ to elevate levels of $NAD^+$ and thus promote cellular health, the bioavailability of these molecules may not be optimal as pharmacological and nutritional agent. Accordingly, there remains a need in the art for agents that elevate cellular levels of $NAD^+$ that possess suitable bioavailability and stability, and are free from adverse effects on $NAD^+$-dependent biological systems.

BRIEF SUMMARY OF THE INVENTION

The invention provides a compound of formula (I):

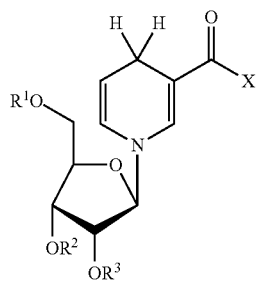

(I)

wherein $R^1$, $R^2$, and $R^3$ are independently selected from hydrogen, formyl, optionally substituted $C_1$-$C_{12}$ alkylcarbonyl, and optionally substituted $C_6$-$C_{10}$ arylcarbonyl, X is $NHR^4$, $NR^4R^5$, or $OR^6$, $R^4$ and $R^5$ are independently optionally substituted $C_1$-$C_{12}$ alkyl or optionally substituted $C_6$-$C_{10}$ aryl, and $R^6$ is hydrogen, optionally substituted $C_1$-$C_{12}$ alkyl, or optionally substituted $C_6$-$C_{10}$ aryl, wherein the alkyl or aryl portion of $R^4$-$R^6$ is optionally substituted with one or more substituents selected from halo, amino, alkyl, alkoxy, aryloxy, hydroxyalkyl, and any combination thereof, or a pharmaceutically acceptable salt thereof.

The invention also provides a process for the preparation of a compound of formula (II):

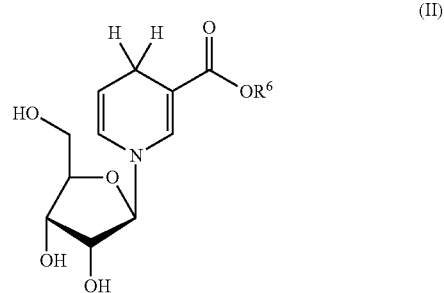

(II)

wherein $R^1$, $R^2$, and $R^3$ are independently selected from hydrogen, formyl, optionally substituted $C_1$-$C_{12}$ alkylcarbonyl, and optionally substituted $C_6$-$C_{10}$ arylcarbonyl, and $R^6$ is hydrogen, optionally substituted $C_1$-$C_{12}$ alkyl, or optionally substituted $C_6$-$C_{10}$ aryl, wherein the alkyl or aryl portion of $R^6$ is optionally substituted with one or more substituents selected from halo, amino, alkyl, alkoxy, aryloxy, hydroxyalkyl, and any combination thereof, wherein the process comprises the steps of:

(i) providing a compound of formula (III):

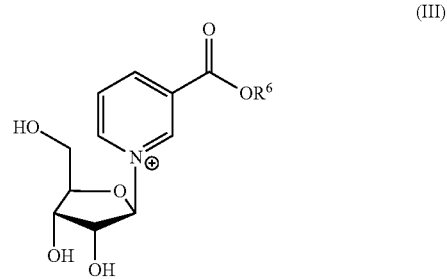

(III)

(ii) reducing the compound of formula (III) with a reducing agent to provide the compound of formula (II), and (iii) isolating the compound of formula (II).

The invention additionally provides a method for increasing cell $NAD^+$ production comprising administering to a cell a compound of formula (I) or a salt thereof.

The invention further provides a method of improving mitochondrial densities in a cell, wherein the method comprises administering to the cell a compound of formula (I) or a salt thereof.

BRIEF DESCRIPTION OF THE SEVERAL VIEWS OF THE DRAWING(S)

DETAILED DESCRIPTION OF THE INVENTION

Figure 1A:
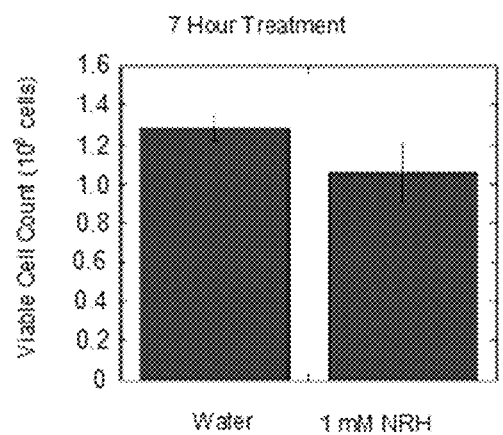
FIG. 1A shows the viable cell counts for HEK293 cells treated with water or dihydronicotinamide riboside.

The invention provides a compound of formula (I):

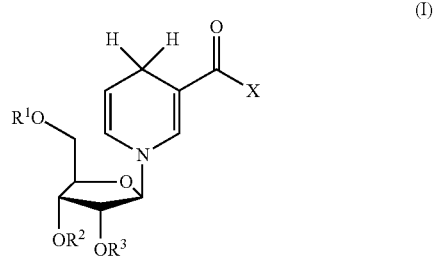

wherein $R^1$, $R^2$, and $R^3$ are independently selected from hydrogen, formyl, optionally substituted $C_1$-$C_{12}$ alkylcarbonyl, and optionally substituted $C_6$-$C_{10}$ arylcarbonyl, X is $NHR^4$, $NR^4R^5$, or $OR^6$, $R^4$ and $R^5$ are independently optionally substituted $C_1$-$C_{12}$ alkyl or optionally substituted $C_6$-$C_{10}$ aryl, and $R^6$ is hydrogen, optionally substituted $C_1$-$C_{12}$ alkyl, or optionally substituted $C_6$-$C_{10}$ aryl, wherein the alkyl or aryl portion of $R^4$-$R^6$ is optionally substituted with one or more substituents selected from halo, amino, alkyl, alkoxy, aryloxy, hydroxyalkyl, and any combination thereof, or a pharmaceutically acceptable salt thereof.

In certain embodiments, when X is $OR^6$ and $R^6$ is hydrogen, $R^1$, $R^2$, and $R^3$ are not all hydrogen or acetyl.

In certain embodiments, X is $OR^6$ and $R^6$ is hydrogen, $R^1$ is not benzoyl and $R^2$ and $R^3$ are not hydrogen.

In certain embodiments, when X is $OR^6$ and $R^6$ is methyl or ethyl, $R^1$, $R^2$, and $R^3$ are not all acetyl.

In certain embodiments, X is $OR^6$, $R^6$ is optionally substituted $C_1$-$C_{12}$ alkyl, and $R^1$, $R^2$, and $R^3$ are hydrogen.

In particular embodiments, the compound is selected from:

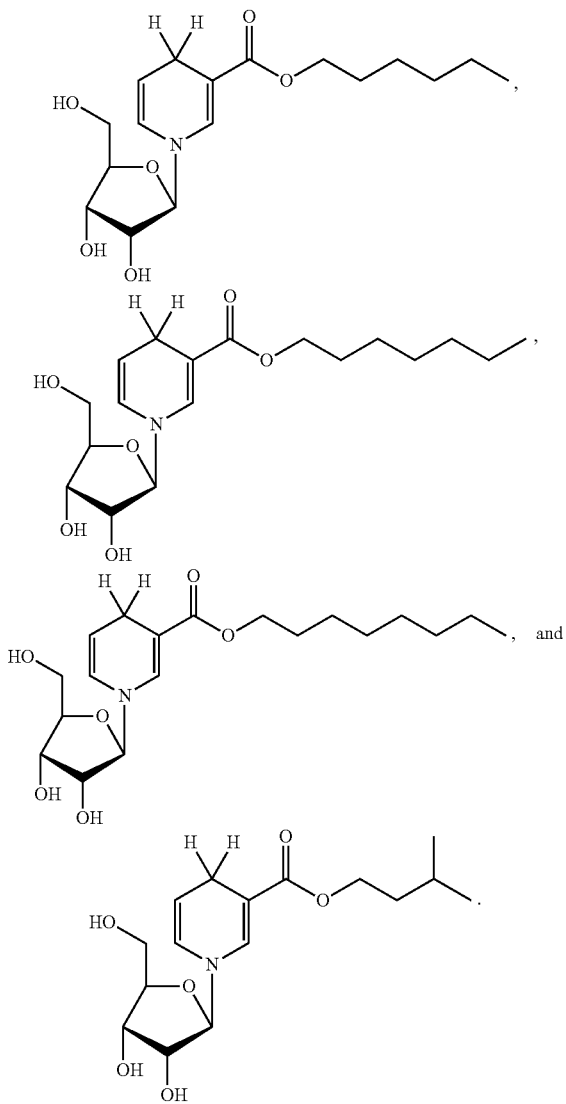

In certain embodiments, X is OR$^6$, R$^6$ is optionally substituted C$_1$-C$_{12}$ alkyl, and R$^1$, R$^2$, and R$^3$ are C$_1$-C$_{12}$ alkylcarbonyl.

In certain embodiments, X is NHR$^4$.

In certain embodiments, X is NR$^4$R$^5$.

In certain of the above embodiments, R$^1$, R$^2$, and R$^3$ are hydrogen.

In certain of the above embodiments, R$^1$, R$^2$, and R$^3$ are C$_1$-C$_{12}$ alkylcarbonyl.

The phrase "salt" or "pharmaceutically acceptable salt" or "salt acceptable for use in dietary supplements or food ingredients" is intended to include nontoxic salts synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two. Generally, nonaqueous media such as ether, ethyl acetate, ethanol, isopropanol, or acetonitrile are preferred. Lists of suitable salts are found in *Remington's Pharmaceutical Sciences,* 18th ed., Mack Publishing Company, Easton, Pa., 1990, p. 1445, and *Journal of Pharmaceutical Science,* 66, 2-19 (1977). For example, they can be a salt of an alkali metal (e.g., sodium or potassium), alkaline earth metal (e.g., calcium), or salt of ammonium or alkylammonium, for example, monoalkylammonium, dialkylammonium, trialkylammonium, or tetraalkylammonium.

Examples of salts for use in the present inventive compositions include those derived from mineral acids, such as hydrochloric, hydrobromic, phosphoric, metaphosphoric, nitric and sulphuric acids, and organic acids, such as tartaric, acetic, citric, malic, lactic, fumaric, benzoic, glycolic, gluconic, succinic, maleic and arylsulfonic acids, for example, methanesulfonic, trifluoromethanesulfonic, benzenesulfonic, and p-toluenesulfonic, acids.

The invention further provides a pharmaceutical composition, a dietary supplement composition, or a food ingredient composition, comprising a compound as described above in any of the embodiments and a pharmaceutically acceptable carrier. The invention provides a pharmaceutical composition comprising a pharmaceutically acceptable carrier and an effective amount, e.g., a therapeutically effective amount, including a prophylactically effective amount, of one or more of the aforesaid compounds, or salts thereof, of the invention. The invention also provides a dietary supplement or food ingredient composition comprising an acceptable carrier and an effective amount, e.g., an amount to affect the structure or function of the body, of one or more of the aforesaid compounds, or salts thereof, of the invention.

The acceptable carrier can be any of those conventionally used and is limited only by chemico-physical considerations, such as solubility and lack of reactivity with the compound, and by the route of administration. It will be appreciated by one of skill in the art that, in addition to the following described pharmaceutical, dietary supplement, or food ingredient compositions; the compounds of the invention can be formulated as inclusion complexes, such as cyclodextrin inclusion complexes, or liposomes.

The acceptable carriers described herein, for example, vehicles, adjuvants, excipients, or diluents, are well known to those who are skilled in the art and are readily available to the public. It is preferred that the acceptable carrier be one which is chemically inert to the active compounds and one which has no detrimental side effects or toxicity under the conditions of use.

The choice of carrier will be determined in part by the particular active agent, as well as by the particular method used to administer the composition. Accordingly, there is a wide variety of suitable formulations of the pharmaceutical, dietary supplement, and food ingredient compositions of the invention. The following formulations for oral, aerosol, parenteral, subcutaneous, intravenous, intraarterial, intramuscular, interperitoneal, intrathecal, rectal, and vaginal administration are merely exemplary and are in no way limiting.

Formulations suitable for oral administration can consist of (a) liquid solutions, such as an effective amount of the compound dissolved in diluents, such as water, saline, or orange juice; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol, and the polyethylene alcohols, either with or without the addition of a pharmaceutically acceptable (or acceptable for dietary supplements or food ingredients) surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and cornstarch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible carriers. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such carriers as are known in the art.

The compounds of the invention, alone or in combination with other suitable components, can be made into aerosol formulations to be administered via inhalation. These aerosol formulations can be placed into pressurized acceptable propellants, such as dichlorodifluoromethane, propane, nitrogen, and the like. They also may be formulated as pharmaceuticals for non-pressured preparations, such as in a nebulizer or an atomizer.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The compound can be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol, glycerol ketals, such as 2,2-dimethyl-1,3-dioxolane-4-methanol, ethers, such as poly(ethyleneglycol) 400, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters. Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylene-polypropylene copolymers, (d) amphoteric detergents such as, for example, alkyl-beta-aminopropionates, and 2-alkyl-imidazoline quaternary ammonium salts, and (3) mixtures thereof.

The parenteral formulations will typically contain from about 0.5 to about 25% by weight of the active ingredient in solution. Suitable preservatives and buffers can be used in such formulations. In order to minimize or eliminate irritation at the site of injection, such compositions may contain one or more nonionic surfactants having a hydrophile-lipophile balance (HLB) of from about 12 to about 17. The quantity of surfactant in such formulations ranges from about 5 to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials, and can be stored in a freeze-dried (lyophilized) condition requiring only the addition of the sterile liquid carrier, for example, water, for injections, immediately prior to use. Extemporaneous injection solutions and suspensions can be prepared from sterile powders, granules, and tablets of the kind previously described.

The compounds of the invention may be made into injectable formulations. The requirements for effective pharmaceutical carriers for injectable compositions are well known to those of ordinary skill in the art. See Pharmaceutics and Pharmacy Practice, J. B. Lippincott Co., Philadelphia, Pa., Banker and Chalmers, eds., pages 238-250 (1982), and *ASHP Handbook on Injectable Drugs*, Toissel, 4th ed., pages 622-630 (1986).

Additionally, the compounds of the invention may be made into suppositories by mixing with a variety of bases, such as emulsifying bases or water-soluble bases. Formulations suitable for vaginal administration may be presented as pessaries, tampons, creams, gels, pastes, foams, or spray formulas containing, in addition to the active ingredient, such carriers as are known in the art to be appropriate.

The invention also provides a dietary supplement or food ingredient composition comprising a compound as described above in any of the embodiments. The terms dietary supplement and food ingredient as used herein denotes the usefulness in both the nutritional field of application. The dietary supplement and food ingredient compositions according to the invention may be in any form that is suitable for administrating to the animal body including the human body, especially in any form that is conventional for oral administration, e.g. in solid form such as (additives/supplements for) food or feed, food or feed premix, tablets, pills, granules, dragees, capsules, and effervescent formulations such as powders and tablets, or in liquid form such as solutions, emulsions or suspensions as e.g. beverages, pastes and oily suspensions. Controlled (delayed) release formulations incorporating the compounds according to the invention also form part of the invention. Furthermore, a multi-vitamin, mineral, or other supplement may be added to the dietary supplement and food ingredient compositions of the invention to obtain an adequate amount of an essential nutrient, which is missing in some diets, or to further aid the structure or function of the body. The multi-vitamin and mineral supplement may also be useful for disease prevention and protection against nutritional losses and deficiencies due to lifestyle patterns.

Chemistry

The compounds of the invention can prepared by any suitable process. For example, the process can comprise the steps of (i) providing a compound of formula (IV):

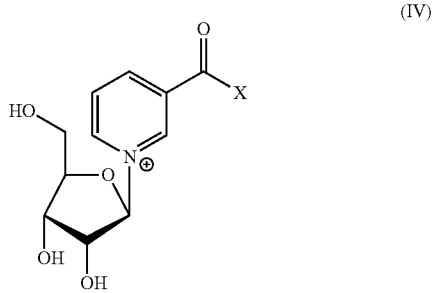

wherein $R^1$, $R^2$, and $R^3$ are independently selected from hydrogen, formyl, optionally substituted $C_1$-$C_{12}$ alkylcarbonyl, and $C_6$-$C_{10}$ optionally substituted arylcarbonyl, X is $NHR^4$, $NR^4R^5$, or $OR^6$, $R^4$ and $R^5$ are independently optionally substituted $C_1$-$C_{12}$ alkyl or optionally substituted $C_6$-$C_{10}$ aryl, and $R^6$ is hydrogen, optionally substituted $C_1$-$C_{12}$ alkyl, or optionally substituted $C_6$-$C_{10}$ aryl, (ii) treating the compound of formula (IV) with a reducing agent to provide the compound of formula (V),

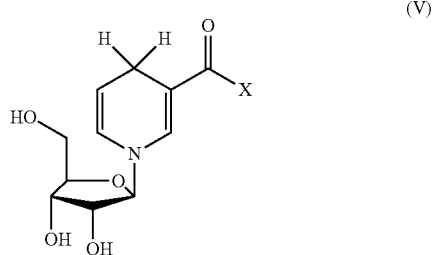

and (iii) isolating the compound of formula (V).

The compound of formula (IV) can be prepared using any suitable process. For example, the compound of formula (IV) can be prepared by processes disclosed in U.S. Patent Application Publication 2007/0117765 A1, the contents of which are totally incorporated herein by reference.

In an embodiment, the invention provides a process for the preparation of a compound of formula (II):

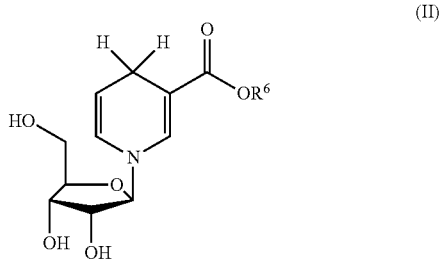

wherein $R^1$, $R^2$, and $R^3$ are independently selected from hydrogen, formyl, optionally substituted $C_1$-$C_{12}$ alkylcarbonyl, and $C_6$-$C_{10}$ optionally substituted arylcarbonyl, and $R^6$ is hydrogen, optionally substituted $C_1$-$C_{12}$ alkyl, or optionally substituted $C_6$-$C_{10}$ aryl, wherein the alkyl or aryl portion of $R^6$ is optionally substituted with one or more substituents selected from halo, amino, alkyl, alkoxy, aryloxy, hydroxyalkyl, and any combination thereof, wherein the process comprises the steps of:

(i) providing a compound of formula (III):

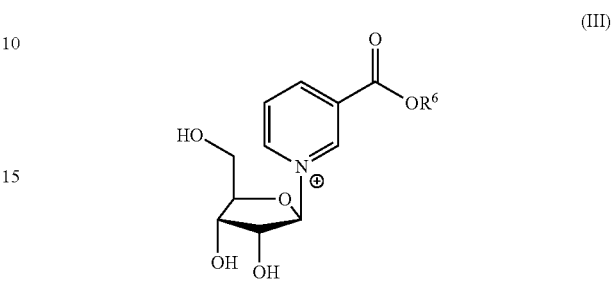

(ii) treating the compound of formula (III) with a reducing agent to provide the compound of formula (II), and (iii) isolating the compound of formula (II).

The reducing agent can be any suitable reducing agent and can be, for example, sodium dithionate, sodium borohydride, hydrogen in the presence of a catalyst, and the like.

Isolation of the compound of formula (II) can be accomplished using any suitable isolation technique. In embodiments, the isolation is conducted by chromatography. Non-limiting examples of suitable chromatographic techniques include normal phase chromatography over silica gel or high performance liquid chromatography (HPLC) over reversed phase supports. In some embodiments, the isolation can be conducted by crystallization from a suitable solvent or mixture of solvents.

Exemplars of the compounds of the invention exhibit a surprising and unexpected effect on mammalian cells vis-a-vis $NAD^+$ increases. These occur at relatively low concentrations and increases in $NAD^+$ in excess of 400% can be obtained at 20-200 microM where other compounds at any concentration are not efficacious to achieve the effect. Because of reduction of the ring, the compounds are also more lipophilic than their respective aromatic relatives, and this may increase absorption and BBB penetration characteristics. The synthetic methods themselves provide the first fully efficient methods to achieve the compounds. The key features of the compounds appear to be potency, ease of access, novelty, lack of literature characterization of the biological properties, evidence for biological efficacy in enhancing $NAD^+$ above previously described molecules, and opportunities for improved drug behavior from enhanced lipophilicity.

In some embodiments, the invention provides a method for increasing mammalian cell $NAD^+$ production comprising administering to a cell a compound of the invention or a pharmaceutically acceptable salt thereof. Nicotinamide adenine dinucleotide (NAD or $NAD^+$) is important as a co-enzyme for different enzymes. Recent studies depicted that being the co-substrate of SIR2 (silent information regulator 2), $NAD^+$ has a role in regulating multiple biological processes, such as p53 regulated apoptosis, fat storage, stress resistance, and gene silencing. Without limiting the potential uses of the compositions described herein by any single theory, there are various pathways through which nicotinamide riboside (NR), dihydronicotinamide riboside (NRH), nicotinic acid riboside (NAR), and dihydronicotinic acid riboside (NARH or NaR-H) and their derivatives are currently thought to be metabolized. NR and NRH are known as NAD$^+$ precursors for both human and yeast. They are able to enter a salvage pathway that leads to biological synthesis of NAD$^+$ under the action of the enzyme nicotinamide riboside kinase (Nrk). Each of NR and NRH can be converted to nicotinamide mononucleotide (NMN) and nicotinic acid mononucleotide (NAMN) by nicotinamide riboside kinases (Nrk), which are then converted to NAD$^+$ by the enzyme nicotinamide mononucleotide adenylytransferase (Nmnat). Alternatively, NR and NRH can enter NAD metabolism by means of other metabolic paths, which would include action from enzymes that separate the nicotinamide moiety from the sugar. Such a path would include the action of phosphorylases that have been shown to degrade NR and NRH in cells to form nicotinamide and ribose-1-phosphate. Nicotinamide is competent to enter NAD$^+$ metabolism and is converted to NAD+ by the action of the enzyme nicotinamide pyrophosphoribosyltransferase. Sirtuins are class III histone deacetylases (HDACs) and are ADP-ribosyl transferases also. They deacetylate lysine residues in a novel chemical reaction that consumes nicotinamide adenine dinucleotide (NAD$^+$), releasing nicotinamide, O-acetyl-ADPribose (AADPR), and the deacetylated substrate. Altering intracellular NAD$^+$ levels can improve the health of a cell, but introduction of compounds that enter NAD$^+$ metabolic pathways can also prove toxic to cells. In some embodiments, the invention relates to the use of compounds disclosed herein to manipulate NAD$^+$ levels, to modulate the activity of sirtuins and other ADP-ribosyl transferases, and to modulate inosine 5'-monophosphate dehydrogenase. These embodiments are used to destroy or weaken the defenses of cancer cells, or to promote survival of neurons, myocytes, or stem cells via addition to growth media.

Nicotinic acid is an effective agent in controlling low-density lipoprotein cholesterol, increasing high-density lipoprotein cholesterol, and reducing triglyceride and lipoprotein (a) levels in humans. Though nicotinic acid treatment affects all of the key lipids in the desirable direction and has been shown to reduce mortality in target populations, its use is limited because of a side effect of heat and redness termed flushing. Further, nicotinamide is neuroprotective in model systems, presumably due to multiple mechanisms including increasing mitochondrial NAD$^+$ levels. NR and derivatives thereof has also proved useful in model systems and in clinical trials in humans in a variety of uses, including promoting healthy aging, supporting and promoting healthy metabolic function, supporting and promoting cognitive function, neuroprotection in CNS and PNS trauma including stroke, and in neurogenerative diseases and conditions including essential tremor, Parkinson disease, Alzheimer disease, Huntington disease, ataxia, catatonia, epilepsy, neuroleptic malignant syndrome, dystonia, neuroacanthocytosis, Pelizaeus-Merzbacher, progressive supranuclear palsy, Striatonigral degeneration, Tardive dyskinesias, or a lysosomal storage disorder, including lipid storage disorders (including Gaucher's and Niemann-Pick diseases), gangliosidosis (including Tay-Sachs disease), leukodystrophies, mucopolysaccharidoses, glycoprotein storage disorders, and mucolipidoses. They have also been found useful to prevent hearing loss due to aging or exposure to loud sounds. They also can protect cells from damage to exposure to toxins, including damage to myocytes caused by statins. They can slow or prevent the death of islet cells that produce insulin. They have also been found to increase the number of, and improve the function of, mitochondria.

NRH or derivatives may be bioavailable and are ultimately convertible by metabolism to nicotinic acid or nicotinamide and to NAD+, thereby providing the benefits of the compounds as discussed above. Accordingly, one embodiment of the invention relates to the use of compositions comprising compounds disclosed herein that work through the nicotinamide riboside kinase pathway or other pathways of NAD$^+$ biosynthesis which have nutritional and/or therapeutic value in improving poor plasma lipid profiles in lipid disorders, (e.g., dyslipidemia, hypercholesterolaemia or hyperlipidemia), metabolic dysfunction in type I and II diabetes, cardiovascular disease, and other physical problems associated with obesity, protecting islet cells to treat or prevent development of diabetes, neuroprotection to treat trauma and neurodegenerative diseases and conditions, protecting muscle cells from toxicity and damage from workouts or trauma, promoting the function of the auditory system, treating or preventing hearing loss, and dietary supplement and food ingredient uses for promoting metabolic function, muscle function and healing/recovery, cognitive function, and mitochondrial function.

In some embodiments, the invention relates to the use of compounds disclosed herein as agonist and antagonist of enzymes in the pathway of NAD$^+$ biosynthesis. In further embodiments, the NHR derivatives disclosed herein are agonist, i.e., stimulates activities normally stimulated by naturally occurring substances, of one or more sirtuins, preferably SIRT1 in humans or Sir2p in yeast. In further embodiments, the NHR derivatives are antagonist of one or sirtuins.

In some embodiments, the invention provides a method of improving metabolic function, including increased mitochondrial densities, insulin sensitivity, or exercise endurance in a mammal, wherein the method comprises administering to the mammal a compound of the invention or a pharmaceutically acceptable salt, or salt acceptable for dietary supplements or food ingredients, thereof. It is known that under calorie restriction, cellular energy depletion causes rising AMP levels, and an increase in the NAD$^+$ level as compared to the reduced level (NADH), results in activation of AMPK. AMPK activation leads to PGC-1alpha activation which leads to mitochondrial biosynthesis (Lopez-Lluch, et al., *Experimental Gerontology*, 2009 September, 43 (9): 813-819 doi:10.1016/j.exger.2008.06.014). Increasing mitochondrial biosynthesis will lead to increased mitochondrial density in the muscle cells. Increased mitochondrial density will increase athletic performance in terms of muscle strength and endurance.

In some embodiments, the invention provides a method of treating or preventing a disease or condition in a mammal in need thereof, wherein the method comprises administering to the mammal a compound of the invention or a pharmaceutically acceptable salt thereof, wherein the disease or condition is CNS or PNS trauma, or a neurodegenerative disease or condition.

NAD$^+$ levels decrease in injured, diseased, or degenerating neural cells and preventing this NAD$^+$ decline efficiently protects neural cells from cell death. Araki & Milbrandt, *Science*, 2004 Aug. 13; 305(5686):1010-3 and Wang et al., "A local mechanism mediates NAD-dependent protection of axon degeneration," *J. Cell Biol.* 170(3): 349-55 (2005), hereby incorporated by reference. As a number of inventive compounds disclosed herein are capable of increasing intracellular levels of NAD$^+$, these compounds are useful as a therapeutic or nutritional supplement in managing injuries, diseases, and disorders effecting the central nervous system and the peripheral nervous system, including but not limited to trauma or injury to neural cells, diseases or conditions that harm neural cells, and neurodegenerative diseases or syndromes. Some neurodegenerative diseases, neurodegenerative syndromes, diseases and conditions that harm neural cells, and injury to neural cells are described above. It is preferred that inventive compounds disclosed herein are capable of passing the blood-brain-barrier (BBB).

In some embodiments, the invention provides a method of protecting a mammal from neurotrauma, wherein the method comprises administering to the mammal a compound of the invention or a pharmaceutically acceptable salt thereof. In certain of these embodiments, the neurotrauma results from blast injury or noise. In these embodiments, the agent increases intracellular $NAD^+$ in one or more cells selected from the group consisting of spiral ganglia nerve cells, hair cells, supporting cells, and Schwann cells.

In certain embodiments, the agent suppresses oxidative damage in the cell. In certain embodiments, the compound activates SIRT3. Endogenous SIRT3 is a soluble protein located in the mitochondrial matrix. Overexpression of SIRT3 in cultured cells increases respiration and decreases the production of reactive oxygen species. Without wishing to be bound by any particular theory, it is believed that activation of SIRT3 is implicated in suppression of oxidative damage in the aforesaid cells.

In certain embodiments, the treating of the mammal with the compound results in prevention of hearing loss. In other embodiments, the treating of the mammal with the agent results in the mitigation of hearing loss. The treating can be performed after exposure to the mammal to circumstances leading to hearing loss, such as exposure to noise, or can be performed prior to exposure of the mammal to the circumstances. The relationship of $NAD^+$ levels and protection from neurotrauma is disclosed in WO 2014/014828 A1, the contents of which are incorporated herein by reference. In certain embodiments, the compound supports the healthy structure or function of the auditory system in a mammal in need thereof. Treating of the mammal with an effective amount of the compound, for example, in a dietary supplement or in a food ingredient composition, augments intracellular $NAD^+$ biosynthesis, wherein intracellular $NAD^+$ increases in spiral ganglia nerve cells, hair cells, supporting cells, Schwann cells, or a combination thereof. In some embodiments, the agent maintains axonal NAD+ levels following axonal injuries caused by acoustic trauma.

Statins, more mechanistically known as 3-hydroxy-3-methyglutaryl coenzyme A reductase inhibitors (or HMG-CoA inhibitors), are some of the world's most widely prescribed drugs. While statins are well tolerated at therapeutic doses, at higher doses and often in combination with other hypolipidaemic agents some potentially severe adverse effects have arisen. Most notably, cerivastatin (Baycol) was removed from the market in 2000 after 31 deaths in the United States from drug-associated rhabdomyolysis (breakdown of muscle fibers resulting in the release of muscle fiber contents into the circulation; some of these are toxic to the kidney) and associated acute renal failure in patients taking cerivastatin. Statins are also known to have severe interactions with fibric acid derivatives, especially with gemfibrozil. Of the 31 people who died taking cerivastatin, 12 were also taking gemfibrozil.

The most serious adverse effects of statins appear to occur in liver and muscle cells, although it could be predicted that because of their lipophilicity, cerebral effects might also be seen in some patients.

The exact mechanism of statin toxicities is unknown. The fact that toxicities are dose-dependent makes plausible the hypothesis that toxicities result from exaggeration of the drug's intended effect: in other words, cells die from lack of the downstream products of HMG-CoA.

HMG-CoA is the rate limiting enzyme in the mevalonate pathway, which, through three branches, leads to the synthesis of cholesterol, dolichol (the precursor to dolichol pyrophosphate, which is the first thing added to proteins in post-translational glycosylation), and to ubiquinone, also known as Coenzyme Q (found in the membranes of endoplasmic reticulum, peroxisomes, lysosomes, vesicles and notably the inner membrane of the mitochondrion where it is an important part of the electron transport chain; it is also has important antioxidant activities).

However, it is likely that depletion of CoQ leads to a breakdown in the electron transport chain, leading in turn to a buildup in NADH, and a depletion in $NAD^+$. Further, the reduced form of CoQ10, CoQ10H2, has an important cellular antioxidant function, which is to protect membranes and plasma lipoproteins against free radical-induced oxidation.

In some embodiments, the invention provides a method of reducing toxicity induced by a HMGCoA reductase inhibitor in a mammal, which method comprises administering to the mammal a therapeutically effective amount of a compound of the invention, wherein the mammal has been administered the HMGCoA reductase inhibitor in an amount that produces toxicity in the mammal in the absence of the administration of the compound of formula (I), and wherein the administration of the compound of claim 1 reduces the toxicity in the mammal. In some embodiments, the invention provides a method of reducing toxicity induced by a HMG-CoA reductase inhibitor in a mammal, which method comprises administering to the mammal a therapeutically effective amount of a compound of the invention and then administering to the mammal the HMGCoA reductase inhibitor in an amount that produces toxicity in the mammal in the absence of the administration of the compound of formula (I), whereby toxicity that would have been induced by the HMGCoA reductase inhibitor is reduced in the mammal by the administration of the compound of the invention. In some embodiments, the invention provides a method of reducing toxicity induced by a HMGCoA reductase inhibitor in a mammal, which method comprises administering to the mammal a therapeutically effective amount of a compound of the invention, whereby toxicity induced by the HMGCoA inhibitor is reduced in the mammal, wherein the compound of the invention is administered to the mammal following manifestation of toxicity by the mammal.

In some embodiments, the invention provides a method of reducing toxicity induced by a genotoxic agent in a mammal, which method comprises administering to the mammal a therapeutically effective amount of a compound of the invention, wherein the mammal has been administered the genotoxic agent in an amount that produces toxicity in the mammal in the absence of the administration of the compound of the invention, and wherein the administration of the compound reduces the toxicity in the mammal. The compound of the invention can be administered to the mammal prior to administration of the genotoxic or other toxic agent to the mammal, simultaneously with administration of the genotoxic or other toxic agent to the mammal, or after administration of the genotoxic or other toxic agent to the mammal, for example, after symptoms of toxicity resulting from administration of the genotoxic or other toxic agent appear in the mammal.

In some embodiments, the invention relates to the use of a compound of the invention to prevent adverse effects and protect cells from toxicity. Toxicity may be an adverse effect of radiation or external chemicals on the cells of the body. Examples of toxins are pharmaceuticals, drugs of abuse, and radiation, such as UV or X-ray light. Both radiative and chemical toxins have the potential to damage biological molecules such as DNA. This damage typically occurs by chemical reaction of the exogenous agent or its metabolites with biological molecules, or indirectly through stimulated production of reactive oxygen species (eg, superoxide, peroxides, hydroxyl radicals). Repair systems in the cell excise and repair damage caused by toxins.

Enzymes that use $NAD^+$ play an part in the DNA repair process. Specifically, the poly(ADP-ribose) polymerases (PARPs), particularly PARP-1, are activated by DNA strand breaks and affect DNA repair. The PARPs consume $NAD^+$ as an adenosine diphosphate ribose (ADPR) donor and synthesize poly(ADP-ribose) onto nuclear proteins such as histones and PARP itself. Although PARP activities facilitate DNA repair, overactivation of PARP can cause significant depletion of cellular $NAD^+$, leading to cellular necrosis. The apparent sensitivity of $NAD^+$ metabolism to genotoxicity has led to pharmacological investigations into the inhibition of PARP as a means to improve cell survival. Numerous reports have shown that PARP inhibition increases NAD+ concentrations in cells subject to genotoxicity, with a resulting decrease in cellular necrosis. Nevertheless, cell death from toxicity still occurs, presumably because cells are able to complete apoptotic pathways that are activated by genotoxicity. Thus, significant cell death is still a consequence of DNA/macromolecule damage, even with inhibition of PARP. This consequence suggests that improvement of $NAD^+$ metabolism in genotoxicity can be partially effective in improving cell survival but that other players that modulate apoptotic sensitivity, such as sirtuins, may also play important roles in cell responses to genotoxins.

Physiological and biochemical mechanisms that determine the effects of chemical and radiation toxicity in tissues are complex, and evidence indicates that $NAD^+$ metabolism is an important player in cell stress response pathways. For example, upregulation of $NAD^+$ metabolism, via nicotinamide/nicotinic acid mononucleotide (NMNAT) overexpression, has been shown to protect against neuron axonal degeneration, and nicotinamide used pharmacologically has been recently shown to provide neuron protection in a model of fetal alcohol syndrome and fetal ischemia. Such protective effects could be attributable to upregulated $NAD^+$ biosynthesis, which increases the available $NAD^+$ pool subject to depletion during genotoxic stress. This depletion of $NAD^+$ is mediated by PARP enzymes, which are activated by DNA damage and can deplete cellular $NAD^+$, leading to necrotic death. Another mechanism of enhanced cell protection that could act in concert with upregulated $NAD^+$ biosynthesis is the activation of cell protection transcriptional programs regulated by sirtuin enzymes.

Examples of cell and tissue protection linked to $NAD^+$ and sirtuins include the finding that SIRT1 is required for neuroprotection associated with trauma and genotoxicity. SIRT1 can also decrease microglia-dependent toxicity of amyloid-beta through reduced NFKB signaling. SIRT1 and increased $NAD^+$ concentrations provide neuroprotection in a model of Alzheimer's disease. Sirtuins are $NAD^+$-dependent enzymes that have protein deacetylase and ADP-ribosyltransferase activities that upregulate stress response pathways. Evidence indicates that SIRT1 is upregulated by calorie restriction and in humans could provide cells with protection against apoptosis via downregulation of p53 and Ku70 functions. In addition, SIRT1 upregulates FOXO-dependent transcription of proteins involved in reactive oxygen species (ROS) detoxification, such as MnSOD. The sirtuin SIRT6 has been shown to participate in DNA repair pathways and to help maintain genome stability.

Pharmacological agents that target both $NAD^+$ metabolism and sirtuins can provide tools to elucidate the involvement of these factors in modulating toxicity-induced tissue damage. Moreover, therapeutic options for treatment of acute and chronic tissue-degenerative conditions can emerge if sirtuins and $NAD^+$ metabolism can be validated as providing enhanced tissue protection. Agents such as the plant polyphenols (eg, resveratrol), the niacin vitamins, and the compound nicotinamide riboside can enhance cell survival outcomes by increasing $NAD^+$ biosynthesis, reducing $NAD^+$ depletion, and/or activating sirtuin enzymes.

The following examples further illustrate the invention but, of course, should not be construed as in any way limiting its scope.

Example 1

This example demonstrates a synthesis of 1-((2R,3S,4R,5R)-3,4-dihydroxy-5-(hydroxymethyl)tetrahydrofuran-2-yl)-1,4-dihydropyridine-3-carboxamide, in accordance with an embodiment of the invention.

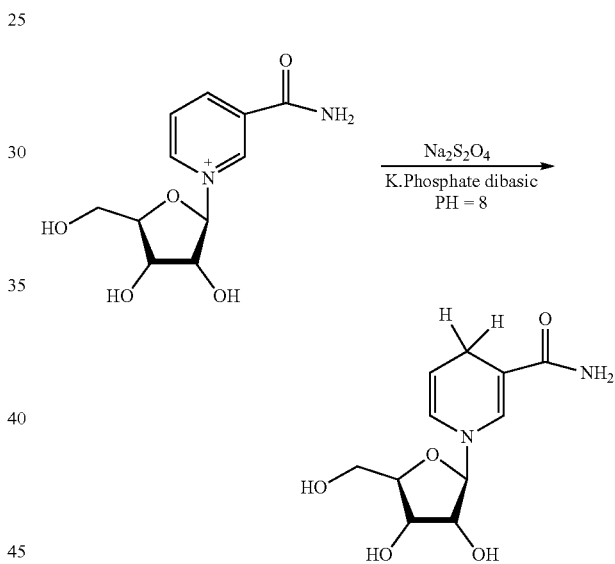

In a flame dried flask under an argon atmosphere, nicotinamide riboside (NR) (100 mg, 0.24 mmol) was added to 10 ml of 50 mM potassium phosphate dibasic (pH=8) at 0° C. After 5 minutes, 0.7 equivalents of sodium dithionate ($Na_2S_2O_4$) were added and then reaction was run at 0° C. for 30 minutes. The progress of the reaction was monitored by HPLC: 70% of starting material was consumed after 30 minutes. The crude product was purified by chromatography over a C-18 column using water as eluent to obtain the title compound as a light yellow solid. Yield 70%.

$^1$H NMR (CD$_3$OD, 500 MHz): δ 7.08 (s, 1H, H-2), 6.02 (d, 1H, J=8.1 Hz, H-6), 4.94-4.89 (m, 1H, H-1'), 4.80 (d, 1H, J=7.1 Hz, H-5), 4.12 (t, 1H, J=6.3 Hz, H-3'), 4.06 (m, 1H, H-4'), 3.90-3.87 (m, 1H, H-2'), 3.69-3.58 (m, 2H, H-5'), 2.99 (s, 2H, H-4a, H-4b). $^{13}$C NMR (CD$_3$OD, 125 MHz): 137.8, 125.2, 105.2, 101.1, 94.9, 83.5, 70.9, 70.1, 61.5, 22.0.

Example 2

(This example demonstrates a synthesis of 2R,3 S,4S, 5R)-2-(acetoxymethyl)-5-(3-(ethoxycarbonyl)pyridin-1

(4H)-yl)tetrahydrofuran-3,4-diyl diacetate, in accordance with an embodiment of the invention.

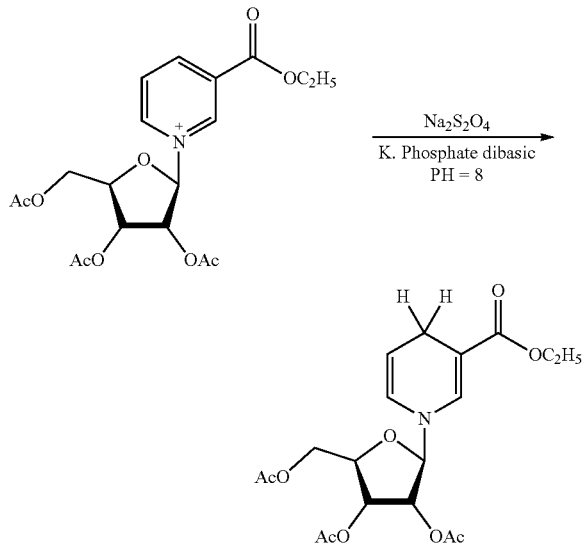

In a flame dried flask under an argon atmosphere, ethyl nicotinate riboside triacetate (200 mg, 0.5 mmol) was added to 20 ml of 50 m M potassium phosphate dibasic (pH=8) at 0° C. After 5 minutes, 0.7 equivalents of sodium dithionate ($Na_2S_2O_4$) were added and the reaction was run at 0° C. for 30 minutes. The progress of the reaction was monitored by HPLC: 60% of starting material was consumed after 30 minutes. The crude product was purified by silica-gel column using ethyl acetate:hexane (3:7) as eluent to obtain the title compound as a light yellow solid. Yield 60%.

$^1$H NMR ($CD_3OD$, 500 MHz): δ 7.28 (s, 1H), 6.05 (dd, 1H, J=1.8 and 9.0 Hz), 5.50 (s, 1H), 5.28-5.25 (m, 1H), 5.22 (t, 1H, J=7.0 Hz), 5.08 (1H, d, J=7.1 Hz), 4.94-4.89 (m, 1H), 4.26-4.24 (m, 1H), 4.20-4.10 (m, 3H), 3.06 (s, 2H), 2.16 (s, 3H). 2.13 (s, 3H), 2.10 (s, 6H): $^{13}$C NMR ($CD_3OD$, 125 MHz): 126.0, 105.2, 100.1, 92.6, 78.6, 70.5, 70.4, 63.8, 60.2, 59.7, 22.6, 21.0, 20.9, 20.7, 14.9.

Example 3

This example demonstrates a synthesis of ethyl-1-((2R, 3S,4R,5R)-3,4-dihydroxy-5-(hydroxymethyl)tetrahydrofuran-2-yl)-1,4dihydropyridine-3-carboxylate, in accordance with an embodiment of the invention.

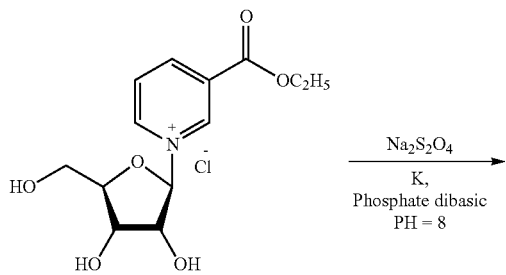

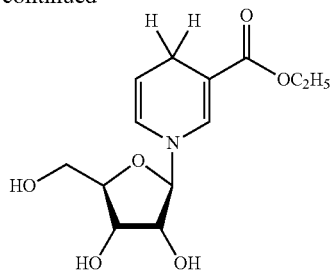

Ethyl nicotinate riboside (200 mg, 0.62 mmol) was added to 25 ml of 50 mM potassium phosphate dibasic (pH=8) at 0° C. After 5 minutes, 75 mg of sodium dithionate ($Na_2S_2O_4$, 0.7 equivalents, 0.43 mmol) were added and the reaction was run at 0° C. for 30 minutes. The progress of the reaction was monitored by HPLC: 70% of starting material was consumed after 30 minutes). The crude product was purified by C-18 column using water as eluent to provide the title compound as a light yellow solid. Yield 65%.

$^1$H NMR ($CD_3OD$, 500 MHz): δ 7.24 (s, 1H, H-2), 5.99 (d, 1H, J=6.9 Hz, H-6), 4.94-4.90 (m, 1H, H-1'), 4.78 (d, 1H, J=6.9 Hz, H-5), 4.14-4.03 (m, 3H), 3.90-3.87 (m, 1H, H-4'), 3.69-3.58 (m, 2H, H2'), 3.26 (s, 1H, H-5'), 2.94 (s, 2H, H-4a, H-4b), 1.17 (t, 3H, —CH3, J=7.0 Hz); $^{13}$C NMR ($CD_3OD$, 125 MHz): 140.9, 124.5, 106.4, 99.2, 94.9, 83.6, 71.0, 70.2, 61.4, 61.0, 21.6, 13.

Example 4

This example demonstrates a synthesis of butyl 1-((2R, 3S,4R,5R)-3,4-dihydroxy-5-(hydroxymethyl)tetrahydrofuran-2-yl)-1,4dihydropyridine-3-carboxylate, in accordance with an embodiment of the invention.

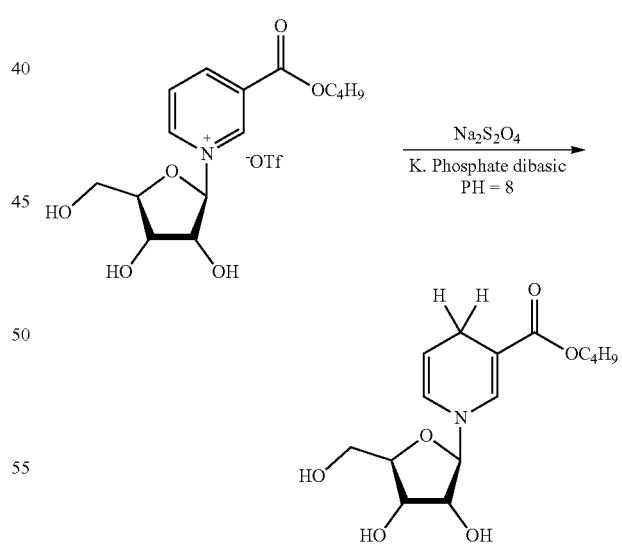

Butyl nicotinate riboside nucleotide (50 mg, 0.10 mmol) was added to 4 ml of 50 mM potassium phosphate dibasic (pH=8) at 0° C. After 5 minutes, 19 mg of sodium dithionate ($Na_2S_2O_4$, 1 eq and 0.10 mmol) was added and the reaction was run at 0° C. for 30 minutes. The progress of the reaction was monitored by TLC: 15% of starting material was consumed after 30 minutes). The water layer was extracted with ethyl acetate. The crude product was purified by silica column using ethyl acetate as eluent to obtain the title compound as a solid. Yield 15%.

$^1$H NMR (CD$_3$OD, 500 MHz): δ 7.30 (s, 1H), 6.13 (d, 1H, J=8.5 Hz), 4.76 (d, 1H, J=7.0 Hz), 4.11 (t, 2H, J=6.9 and 13.8 Hz), 4.07-4.01 (m, 2H), 3.89-3.86 (m, 1H), 3.73-3.62 (m, 3H), 3.07 (s, 2H), 1.68-1.61 (m, 2H), 1.47-1.39 (m, 2H), 0.97 (t, 3H. J=7.5 and 14.4 Hz). $^{13}$C NMR (CD$_3$OD, 125 MHz): 169.0, 152.6, 149.7, 140.2, 137.5, 125.2, 123.9, 104.6, 98.2, 95.9, 84.3, 72.0, 70.7, 65.1, 63.4, 61.9, 30.7, 22.1, 18.9, 12.7.

Example 5

This example demonstrates a synthesis of 1-(1-((2R,3S,4R,5R)-3,4-dihydroxy-5-(hydroxymethyl)tetrahydrofuran-2-yl)-1,4-dihydropyridin-3-yl)octan-1-one, in accordance with an embodiment of the invention.

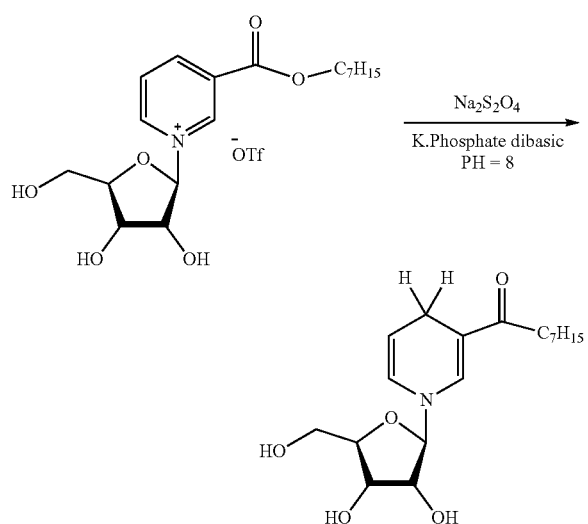

Heptyl nicotinate riboside (50 mg, 0.10 mmol) was added to 4 ml of 50 mM potassium phosphate dibasic (pH=8) at 0° C. After 5 minutes, 18 mg of sodium dithionate (Na$_2$S$_2$O$_4$, 1 equivalent, 0.10 mmol) was added and the reaction was run at 0° C. for 30 minutes. The progress of the reaction was monitored by TLC: 15% of starting material was consumed after 30 minutes). The water layer was extracted with 15 ml ethyl acetate. The ethyl acetate layer was concentrated and the crude product was purified by silica column using ethyl acetate as eluent to obtain the title compound as a solid. Yield 15%.

$^1$H NMR (CD$_3$OD, 500 MHz): δ 7.99 (s, 1H), 6.13 (d, 1H, J=8.3 Hz), 4.76 (d, 1H, J=6.6 Hz), 4.10 (t, 2H, J=6.3 and 13.2 Hz), 4.07-4.02 (m, 2H), 3.89-3.86 (m, 1H), 3.73-3.62 (m, 2H), 3.08-3.05 (m, 2H), 1.70-1.63 (m, 2H), 1.43-1.29 (m, 9H), 0.95-0.89 (m, 3H). $^{13}$C NMR (CD$_3$OD, 125 MHz): 146.6, 143.6, 140.2, 128.0, 125.1, 104.6, 101.3, 98.2, 95.9, 89.9, 84.3, 78.7, 72.2, 70.9, 70.7, 66.9, 66.8, 65.0, 63.7, 61.9, 31.5, 28.7, 28.3, 25.7, 25.5, 22.3, 22.1, 13.0.

Example 6

This example demonstrates a synthesis of 1-(1-((2R,3S,4R,5R)-3,4-dihydroxy-5-(hydroxymethyl)tetrahydrofuran-2-yl)-1,4-dihydropyridin-3-yl)nonan-1-one, in accordance with an embodiment of the invention.

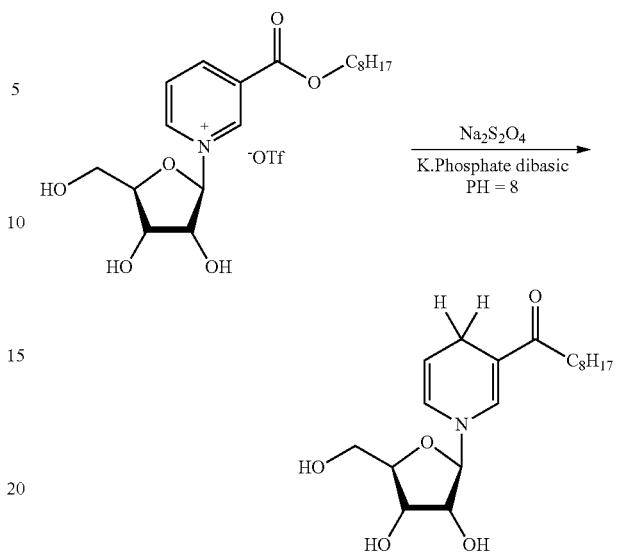

Octyl nicotinate riboside (50 mg, 0.10 mmol) was added to 4 ml of 50 mM potassium phosphate dibasic (pH=8) at 0° C. After 5 minutes, 20 mg of sodium dithionate (Na$_2$S$_2$O$_4$, 1 equivalent and 0.10 mmol) was added and the reaction was run at 0° C. for 30 minutes. The progress of the reaction was monitored by TLC: 1 5% of starting material was consumed after 30 minutes). The water layer was extracted with ethyl acetate. The crude product was purified by silica column using ethyl acetate as eluent to obtain the title compound as a solid. Yield 15%.

$^1$H NMR (CD$_3$OD, 500 MHz): δ 7.29 (s, 1H), 6.13 (d, 1H, J=8.4 Hz), 4.76 (d, 1H, J=6.0 Hz), 4.10 (t, 2H, J=5.4 and 11.7 Hz), 4.07-4.02 (m, 2H), 3.89-3.86 (m, 1H), 3.73-3.62 (m, 2H), 3.34-3.31 (m, 2H), 3.08-3.05 (m, 2H), 1.69-1.62 (m, 2H), 1.46-1.03 (m, 8H), 0.98-0.90 (m, 4H). $^{13}$C NMR (CD$_3$OD, 125 MHz): 169.0, 140.2, 125.1, 104.6, 98.2, 95.9, 89.9, 78.7, 72.0, 71.0, 70.7, 66.9, 66.8, 65.0, 63.7, 61.9, 61.6, 60.5, 32.3, 31.6, 29.2, 29.1, 29.0, 28.6, 25.8, 25.6, 22.3, 22.1, 13.0.

Example 7

This example demonstrates a synthesis of methyl-1-((2R,3S,4R,5R)-3,4-dihydroxy-5-(hydroxymethyl)tetrahydrofuran-2-yl)-1,4-dihydropyridine-3-carboxylate, in accordance with an embodiment of the invention.

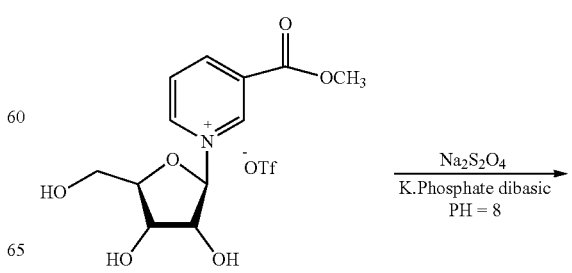

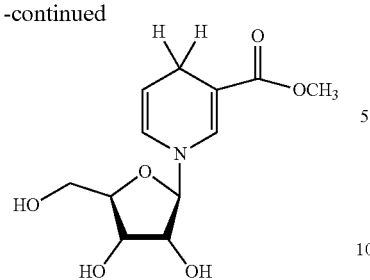

Methyl nicotinate riboside (200 mg, 0.47 mmol) was added to 20 ml of 50 m M potassium phosphate dibasic (pH=8) at 0° C. After 5 minutes, 57 mg of sodium dithionate ($Na_2S_2O_4$, 0.7 equivalent, 0.32 mmol) was added and the reaction was run at 0° C. for 30 minutes. The progress of the reaction was monitored by HPLC: 15% of starting material was consumed after 30 minutes. The crude product was purified by silica column using ethyl acetate as eluent to obtain the title compound as a solid. Yield 15%.

$^1$H NMR ($CD_3OD$, 500 MHz): δ 7.27 (s, 1H, H-2), 6.00 (d, 1H, J=7.5 Hz, H-6), 4.95-4.92 (m, 1H, H-1'), 4.80-4.78 (m, 1H, H-5), 4.12 (t, 1H, J=5.8 and 12.9 Hz, H-3'), 4.06-4.04 (m, 1H, H-4'), 3.98 (m, 1H, H-2'), 3.91-3.87 (m, 2H, H-5'), 3.64-3.62 (s, 3H, OCH3).

Example 7

This example demonstrates a synthesis of isopentyl 1-((2R,3S,4R,5R)-3,4-dihydroxy-5-(hydroxymethyl)tetrahydrofuran-2-yl)1,4-dihydropyridine-3-carboxylate, in accordance with an embodiment of the invention.

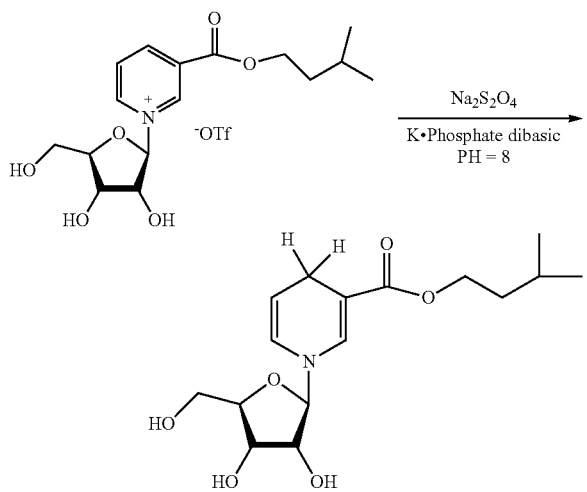

Isoamyl nicotinate riboside (50 mg, 0.10 mmol) was added to 4 ml of 50 mM potassium phosphate dibasic (pH=8) at 0° C. After 5 minutes, 20 mg of sodium dithionate ($Na_2S_2O_4$, 1 equivalent, 0.10 mmol) was added and the reaction was run at 0° C. for 30 minutes. The progress of the reaction was monitored by TLC: 15% of starting material was consumed after 30 minutes. The water layer was extracted with 15 ml ethyl acetate. The crude product was purified by silica column using ethyl acetate as eluent to obtain the title compound as a solid. Yield 15%.

$^1$H NMR ($CD_3OD$, 500 MHz): δ 7.29 (s, 1H), 6.13 (d, 1H, J=6.3 Hz), 4.75 (d, 1H, J=6.3 Hz), 4.43 (t, 1H, J=7.0 and 15.5 Hz), 4.14 (t, 2H, J=6.0 and 14.4 Hz), 4.07-3.99 (m, 1H), 3.89-3.85 (m, 1H), 3.73-3.62 (m, 2H), 3.06 (s, 2H), 1.59-1.53 (m, 2H), 1.05-0.99 (m, 2H), 0.98-0.91 (m, 6H).

Example 8

Methods
Cell Culture

HEK293 and Neuro2A cells were cultured in Dulbecco's modified Eagle's medium supplemented with 10% fetal bovine serum, 100 U/ml penicillin and 100 µg/ml streptomycin. INS1 cells were maintained in RPMI-1640 with 11.1 mmol/l D-glucose supplemented with 10% fetal bovine serum, 100 U/ml penicillin and 100 µg/ml streptomycin, 10 mmol/l HEPES, 2 mmol/l L-glutamine, 1 mmol/l sodium pyruvate, and 50 µmol/l 2-mercaptoethanol. Cells were maintained in a humidified incubator supplied with 5% CO2/95% air at 37° C.

NRH Treatment for $NAD^+$ Measurement

For $NAD^+$ measurement, cells were seeded in 6-well plate for overnight. Then they were treated with desired concentration of NRH from concentrated stock dissolved in water and harvested with trypsin digestion after treatment time. Cell number were counted using hemocytometer. The harvested cells were pelleted at 3000x g for 3 min. After removing the remaining media, cells were lysed with 7% perchloric acid to preserve NAD+, then neutralized with 2M NaOH and 500 mM $K_2HPO_4$. The cellular $NAD^+$ level was measured using as previously published by our lab.

HEK Treated with Reduced NaR Esters.

HEK cells treated with reduced NaR esters (50 µM, 100 µM and 500 µM), Propyl NaR-H (50 µM, 100 µM and 500 µM) and NRH (50 µM and 500 µM) as positive controls. After 6 hours of incubation, cells were harvested with Trypsin. A cell count was obtained from each cell suspension by hemacytometer. The cell pellets were used for $NAD^+$ measurement. The results clearly show that NaR esters increase NAD concentrations.

Glucose-Induced Insulin Secretion Test in INS1 Cells

To induce insulin secretion, INS1 cells were seeded in 6-well plate. The cells were accommodated to low glucose RPMI-1640 media with 5 mmol/l D-glucose overnight. Insulin secretion was assayed in HEPES balanced salt solution (HBSS) (114 mmol/l NaCl, 4.7 mmol/l KCl, 1.2 mmol/l $KH_2PO_4$, 1.16 mmol/l $MgSO_4$, 20 mmol/l HEPES, 2.5 mmol/l $CaCl_2$, 25.5 mmol/l $NaHCO_3$, and 0.2% bovine serum albumin [essentially fatty acid free], pH 7.2). Cells were washed in 1 ml HBSS with 3 mmol/l glucose followed by a 2 hr preincubation in 2 ml of the same buffer. Insulin secretion was then measured by incubating 1 hr 1 ml of HBSS containing the 3 mmol/l or 15 mmol/l glucose concentration. The media was then collected for insulin analysis using RayBio™ Rat Insulin ELISA kit according to manufacturer's manual. In hydrogen peroxide challenge, 100 µM hydrogen peroxide were added to media together with 3 mmol/l glucose containing HBSS and incubated for 2 hr before switch to 15 mmol/l glucose containing HBSS for insulin secretion. 1 mM NRH or NR has been added to low glucose RPMI-1640 media for overnight and replenished when cells were incubated with HBSS.

Mitochondrial Isolation

To measure the individual $NAD^+$ level in mitochondrial and cytoplasm, Neuro2a cells were seeded in 10 $cm^2$ petri dish, then treated with 1 mM NRH for overnight. The cells were harvested with trypsin and pelleted by spinning at 3000x g for 5 min. The mitochondrial fractions were isolated using Mitochondrial Isolation Kit for Mammalian Cells (Thermo Scientific) according to manufacturer's manual. Protein concentrations were later measured using Bradford assay for normalization.

Cytotoxicity Test

To test the effect of NRH against different toxins, Neuro2a, HEK293 or INS1 cells were seeded in 6-well plate and grow until confluent. 500 μM hydrogen peroxide, 400 μM MMS, or 100 nM vincristine was added to media with or without the co-incubation of 1 mM NRH. Cells were harvested after 7 hr with trypsin and used for $NAD^+$ measurement. Trypan blue was used to distinguish dead and live cells during cell count.

Stability Test of NRH

To assess the stability of NRH in different pH environment, 1 mM NRH was incubated in 150 mM phosphate buffer at pH 6, 7, 7.4, 8, and 9, and was injected into EC 250/4.6 Nucleosil 100-5 C18 column on a Hitachi Elite Lachrom™ HPLC system equipped with Diode Array Detector L-2450 after 1, 4, 7 and 10 hr. The incubation temperature on HPLC has been set to 10° C. The C18 column was eluted with 20 mM ammonium acetate at 1 mL/min for 25 min, then with 20 mM ammonium acetate and 20% Methanol for 20 min. NRH was characterized by its peak at 340 nm. The peaks were quantified and used for calculation.

Example 9

This example demonstrates the effect of dihydronicotinamide riboside (NRH) on HEK293 and Neuro2A cell counts.

Figure 1B:
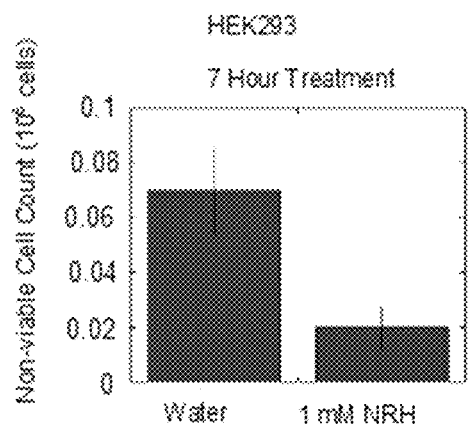
FIG. 1B shows the viable cell counts for Neuro2A cells treated with water or dihydronicotinamide riboside.
Figure 1C:
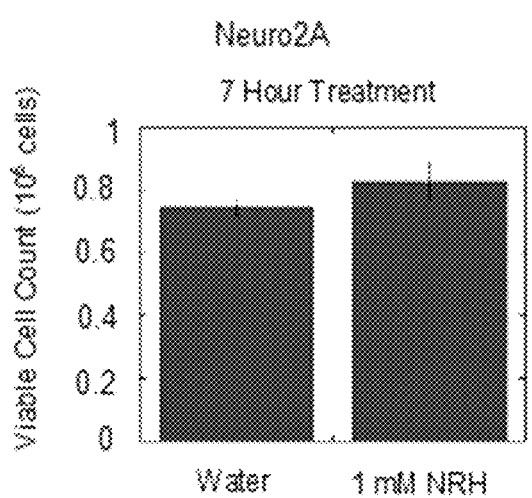
FIG. 1C shows the non-viable cell counts for HEK293 cells treated with water or dihydronicotinamide riboside.
Figure 1D:
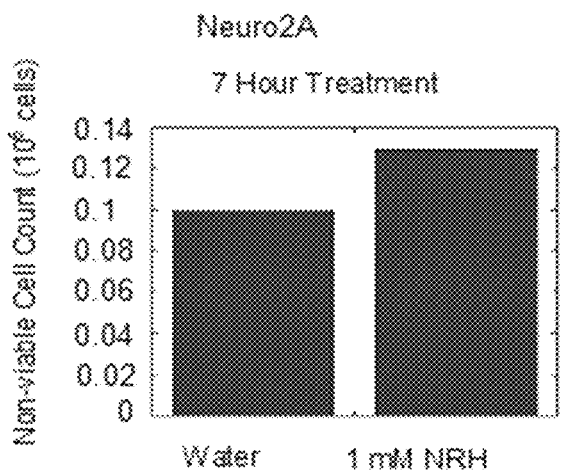
FIG. 1D shows the non-viable cell counts for Neuro2A cells treated with water or dihydronicotinamide riboside.

Cells were seeded into tissue culture coated 6-well plates and grown for 18 hours in complete media (DMEM, 10% FBS) (HEK293: seeded 0.8 million cells per well; Neuro2A: seeded 0.6 million cells per well). Cells were then treated with NRH (1 mM) or equivalent volume of sterile water in complete media for 7 hours. Media was aspirated and cells were suspended in fresh complete media and stained with 0.2% trypan blue for counting by hemacytometer. FIGS. 1A and 1B shows the viable (unstained) cell counts for both HEK293 and Neuro2A cells treated with water or NRH. FIGS. 1C and 1D shows the non-viable (stained) cell counts for both HEK293 and Neuro2A cells treated with water or NRH. Treatment with NRH does not appear to affect cell viability or growth as compared to the water-only controls. The non-viable cell counts are also reduced, suggesting NRH has cell maintenance effects.

Example 10

This example demonstrates the effect on NAD+ levels in HEK293 cells resulting from treatment with dihydronicotinamide riboside (NRH) as compared to treatment with water and with nicotinamide riboside (NR).

Figure 2A:
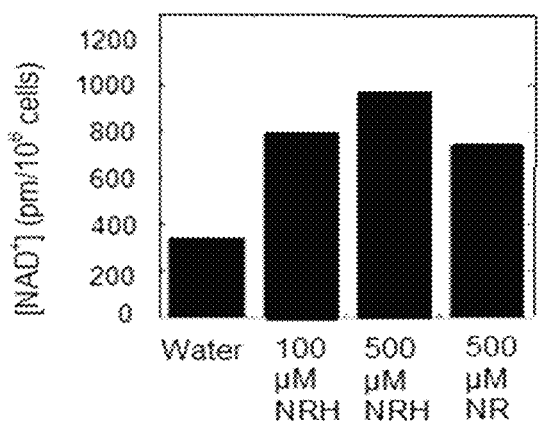
FIG. 2A shows NAD$^+$ levels resulting from a 16 hour treatment of HEK293 cells with water, 100 μM NRH, 500 μM dihydronicotinamide riboside, and 500 μM nicotinamide riboside.
Figure 2B:
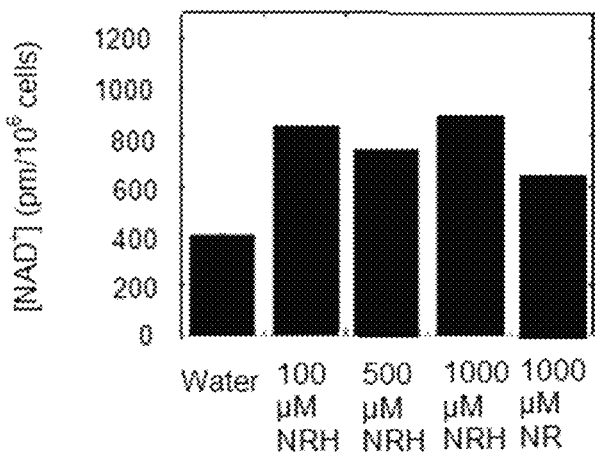
FIG. 2B shows NAD$^+$ levels resulting from an 8 hour treatment of HEK293 cells with water, 100 μM dihydronicotinamide riboside, 500 μM, 1000 μM dihydronicotinamide riboside, and 1900 μM nicotinamide riboside.
Figure 2C:
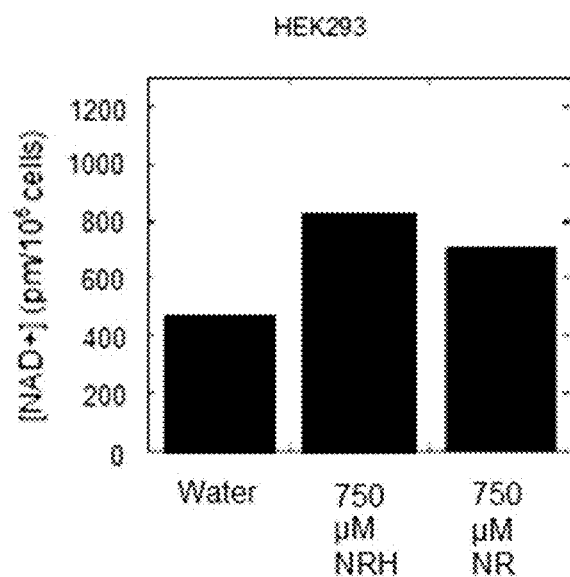
FIG. 2C shows NAD$^+$ levels resulting from a 16 hour treatment of HEK293 cells with water, 750 μM dihydronicotinamide riboside, and 750 μM nicotinamide riboside.

HEK293 cells were grown to 100% confluence in tissue culture treated 6-well plates in complete media (DMEM, 10% FBS). Cells were treated with 100 uM-1 mM NRH for 6 or 16 hours in complete media. Water-only and nicotinamide riboside (NR) control treatments were run. Cells were harvested and NAD+ levels were measured using the NAD+ cycling assay. $NAD^+$ levels are reported in pmol per $10^6$ cells. NAD+ levels resulting from a 16 hour treatment of HEK293 cells with water, 100 μM NRH, 500 μM NRH, and 500 μM NR are shown in FIG. 2A. $NAD^+$ levels resulting from an 8 hour treatment of HEK293 cells with water, 100 μM NRH, 500 μM, 1000 μM RNH, and 1900 μM NR are shown in FIG. 2B. $NAD^+$ resulting from a 16 hour treatment of HEK293 cells with water, 750 μM NRH, and 750 μM NR are shown in FIG. 2C. Across all time points and concentrations, cells treated with NRH had increased $NAD^+$ levels with magnitudes ranging from 76% to 176% increase in NAD+ over water-only controls. Untreated cells were found to have $NAD^+$ levels consistent with a previously reported value for HEK293 cells of 320 pmol/$10^6$ cells. In all cases NRH had a greater effect on $NAD^+$ levels as compared to the NR control.

Example 11

This example demonstrates the effect on $NAD^+$ levels in Neuro2A cells resulting from treatment with dihydronicotinamide riboside (NRH) as compared to treatment with water and with nicotinamide riboside (NR).

Figure 3A:
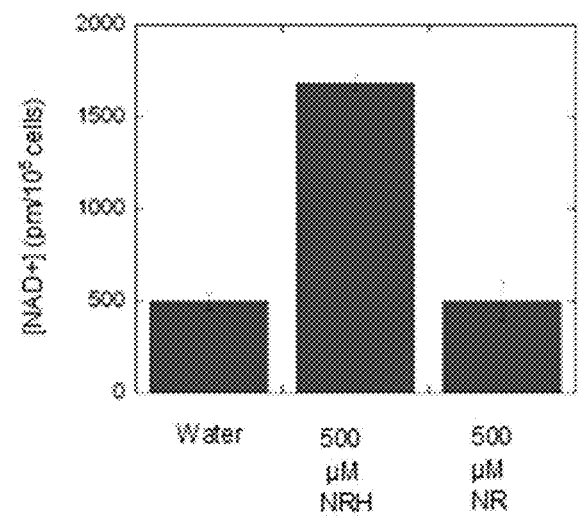
FIG. 3A shows NAD$^+$ levels resulting from treatment of Neuro2A cells with water, 500 μM dihydronicotinamide riboside, and 500 μM nicotinamide riboside.
Figure 3B:
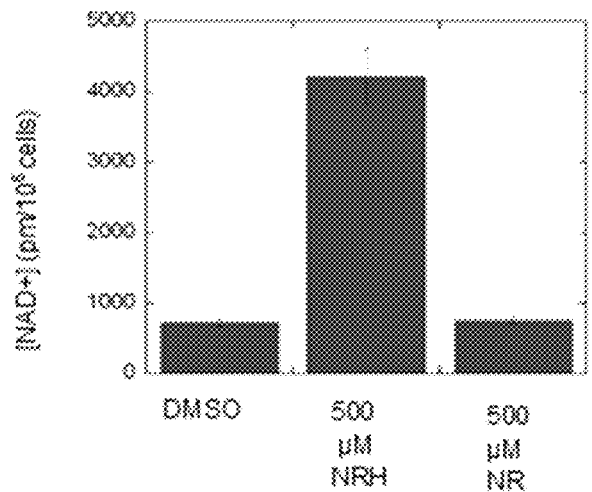
FIG. 3B shows NAD$^+$ levels resulting from treatment of Neuro2A cells with DMSO, 500 μM dihydronicotinamide riboside, and 500 μM nicotinamide riboside.

Neuro2A cells were grown to 100% confluence in tissue culture treated 6-well plates in complete media (DMEM, 10% FBS). Cells were treated with 500 uM NRH for 6 hours in complete media. DMSO-only, water-only and NR control treatments were run. Cells were harvested and NAD+ levels were measured using the $NAD^+$ cycling assay. $NAD^+$ levels are reported in pmol per $10^6$ cells. In FIG. 3A, cells treated with NRH showed a 484% increase in $NAD^+$ levels over the untreated control. In FIG. 3B, NRH treatment gave a 236% increase in $NAD^+$ levels. Untreated cells were found to have $NAD^+$ levels consistent with a previously reported value for Neuro2A cells of 680 pmol/$10^6$ cells.

Example 12

This example demonstrates the effect of treatment with Neuro2A cells with hydrogen peroxide and dihydronicotinamide riboside (NRH).

Figure 4:
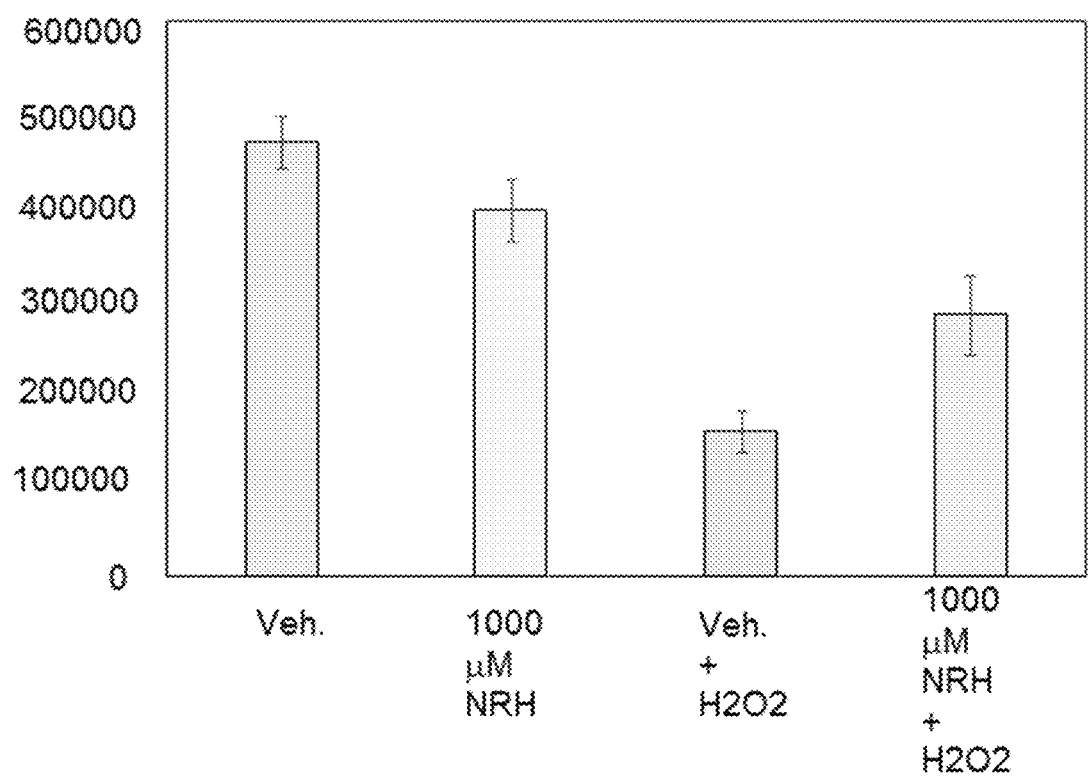
FIG. 4 shows cell counts for Neuro2A cells treated with vehicle, 1000 μM dihydronicotinamide riboside, vehicle+hydrogen peroxide, and 1000 μM dihydronicotinamide riboside+hydrogen peroxide.

Neuro2A cells were grown to 100% confluence in tissue culture treated 6-well plates in complete media (DMEM, 10% FBS). Cells were treated with 1000 uM NRH (columns 2 and 4 of FIG. 4 from left to right) or vehicle (columns 1 and 3 of FIG. 4) for 7 hours in complete media. Lanes 3 and 4 of FIG. 4 show cells that were cotreated with 500 uM hydrogen peroxide. Cells were harvested and viable cells were counted by haemocytometer. The results are shown in FIG. 4. Statistical significance was achieved between columns 1 and 3, and 3 and 4 ($p<0.05$). This result shows that NRH can rescue cells subject to a cell killing stress, meant to mimic physiologically relevant tissue killing stress.

Example 13

This example demonstrates that dihydronicotinamide riboside (NRH) enhances $NAD^+$ levels in different cell types To test if NRH can increase cellular $NAD^+$ level among different mammalian cell types, 1 mM NRH was used to treat neuronal cells (Neuro2a, U87, F98 and LN229), kidney cells (HEK293), muscle cells (C2Cl2) and beta cells (INS1 and MIN6) for 7 hr. NRH has shown robust $NAD^+$ enhancing effect in all tested cell lines, especially in Neuro2a cells where $NAD^+$ level was raised up to around 10 fold comparing to untreated control. The results are set forth in Table 1.

TABLE 1

| Cell Type | Cell Line | Percentage NAD+ increase by 1 mM NRH |
|---|---|---|
| Neuronal cells | Neuro2A | 979% ± 63% |
| | U87 | 659% ± 76% |
| | F98 | 355% ± 45% |
| | LN229 | 386% ± 90% |

TABLE 1-continued

| Cell Type | Cell Line | Percentage NAD+ increase by 1 mM NRH |
|---|---|---|
| Kidney cells | HEK293 | 382% ± 48% |
| Muscle cells | C2C12 | 611% ± 40% |
| Beta cells | INS1 | 299% ± 34% |
| | MIN6 | 384% ± 32% |

Example 14

This example demonstrates that NRH enhances $NAD^+$ levels in a time-dependent and dose-dependent manner.

Figure 5:
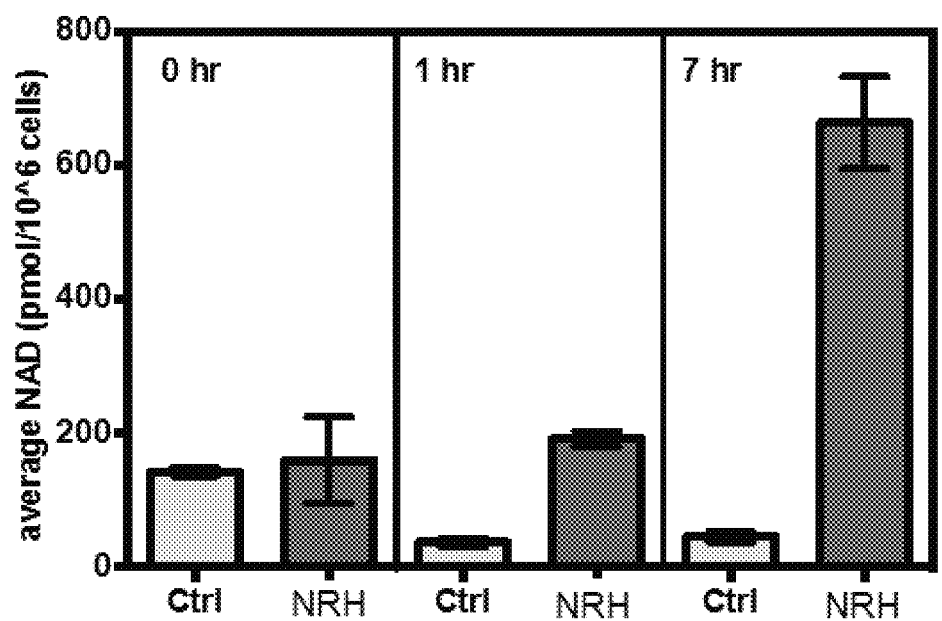
FIG. 5 shows the average NAD$^+$ concentration in Nuero2A cells treated with water or dihydronicotinamide riboside at 0 h, 1 h, and 7 h.
Figure 6:
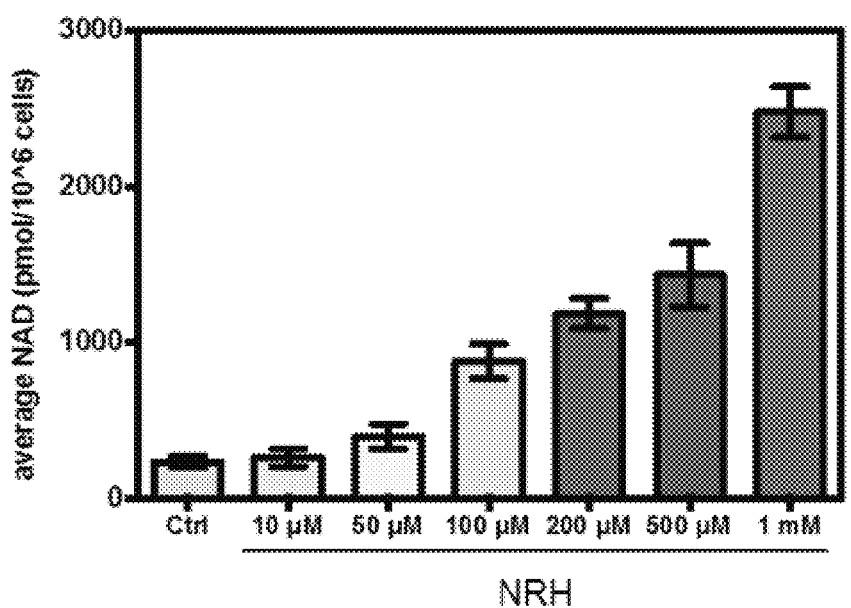
FIG. 6 shows cellular NAD$^+$ levels in Neuro2A cells treated with increasing concentrations of dihydronicotinamide riboside.

In order to assess if the impact of NRH on $NAD^+$ level is time-dependent, Neuro2a cells were treated with 1 mM NRH for 0, 1 or 7 hr. Within 1 hour $NAD^+$ contents increased by 20%, whereas at 7 hours, NRH treatment increased by 400% comparing to control, suggesting that the effect of NRH increasing with incubation time (FIG. 5). Also, to test if NRH has dose-dependent effect, Neuro2a cells were incubated with NRH between 10 to 1000 µM for 7 hour. The cellular $NAD^+$ levels were raised by 121% with 10 µM NRH and escalated gradually as the treatment concentration increased (FIG. 6). These results were further confirmed by HPLC showing higher $NAD^+$ peak in cell lysates from $NAD^+$ treated cells. These data suggest the effect of NRH in Neuro2a cells are both time and dose-dependent.

Example 15

This example demonstrates that NRH has a dose-dependent $NAD^+$ enhancing effect in INS1 cells.

Figure 7:
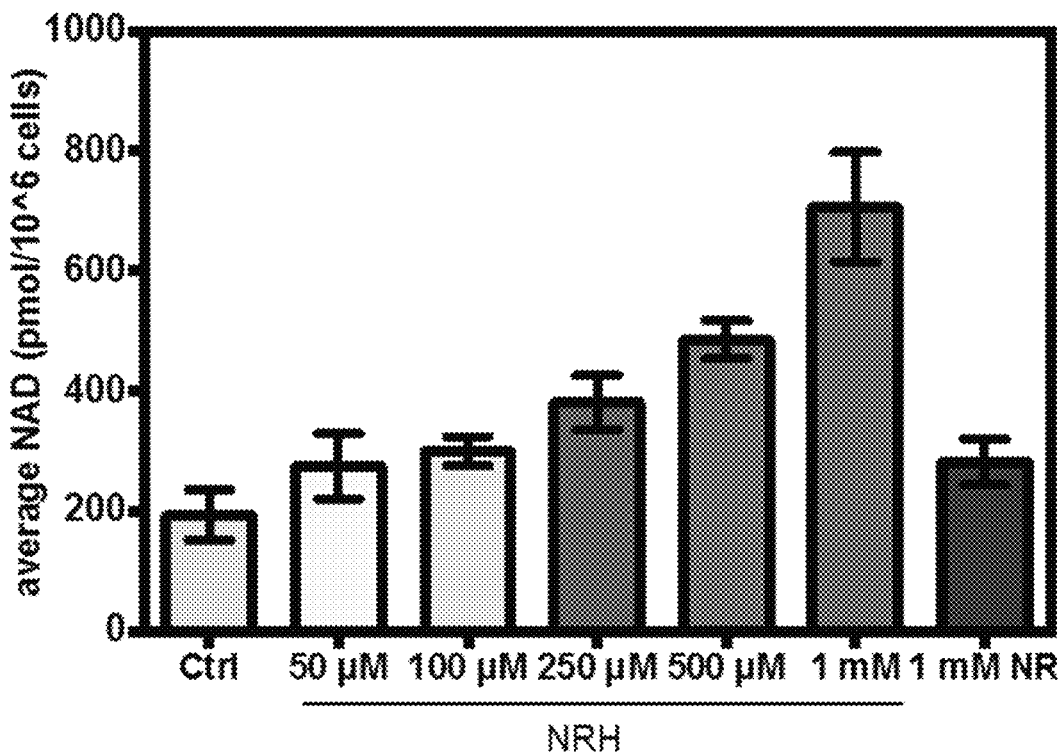
FIG. 7 shows cellular NAD$^+$ levels in INS1 cells treated with increasing concentrations of dihydronicotinamide riboside.

The dose-dependent effect of NRH was tested in INS1 cells for 7 hours. $NAD^+$ levels were gradually increased by elevating NRH concentration in the treatment. The effect of NRH was compared with 1 mM NR. 100 µM NRH exerted similar $NAD^+$ increase as 1 mM NR treatment (FIG. 7), showing that NRH was a stronger $NAD^+$ enhancer comparing to NR in INS1 cells.

Example 16

This example demonstrates that NRH has dose-dependent $NAD^+$ enhancing effect in primary neurons.

Figure 8:
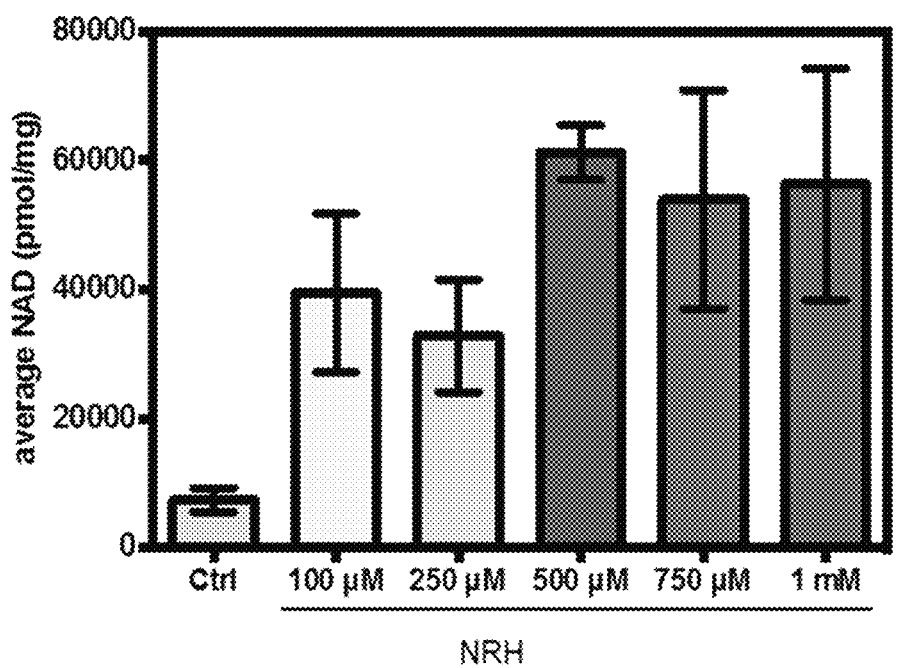
FIG. 8 shows cellular NAD$^+$ levels in primary neuron cells treated with increasing concentrations of dihydronicotinamide riboside.

To test if NRH has similar effect in primary cells as immortalized cell lines, primary neurons cells harvested from rat brains were treated with 100 µM to 1 mM NRH for 6 hr. The primary neurons respond to 100 µM NRH treatment with 4.9 fold increase in their $NAD^+$ levels but the $NAD^+$ levels maximized with 500 µM NRH treatment, by which $NAD^+$ were increased by around 8 fold, as shown in FIG. 8.

Example 17

This example demonstrates that NRH elevated $NAD^+$ level in both mitochondria and cytoplasm.

Figure 9:
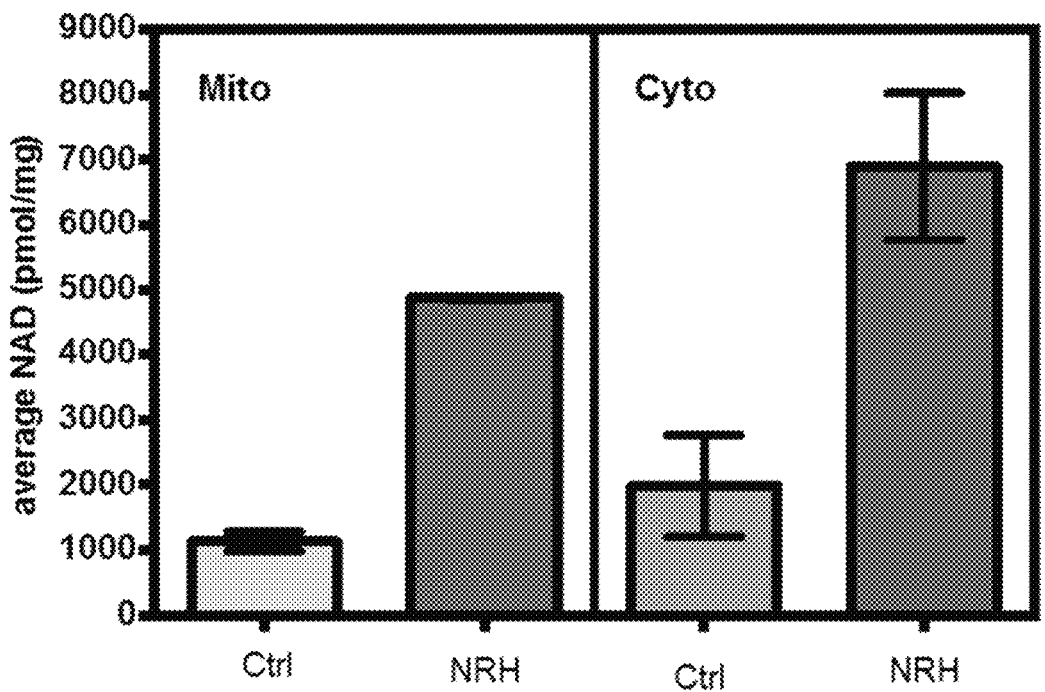
FIG. 9 shows the average concentration of NAD$^+$ in the mitochondria and cytoplasm of Neuro2A cells treated with dihydronicotinamide riboside.

It was evaluated if the $NAD^+$ enhancing effect of NRH is restricted to cell compartment. Neuro2a cells were treated with 1 mM NRH overnight and their mitochondria and cytoplasm were separated for $NAD^+$ analyses. NRH elevated the $NAD^+$ level not only in cytoplasm but also in mitochondria, as shown in FIG. 9, suggesting NRH may have potential benefits in supporting mitochondrial biogenesis by supplying $NAD^+$ directly to mitochondria.

Example 18

This example demonstrates that NRH is stable in alkaline buffer.

Figure 10:
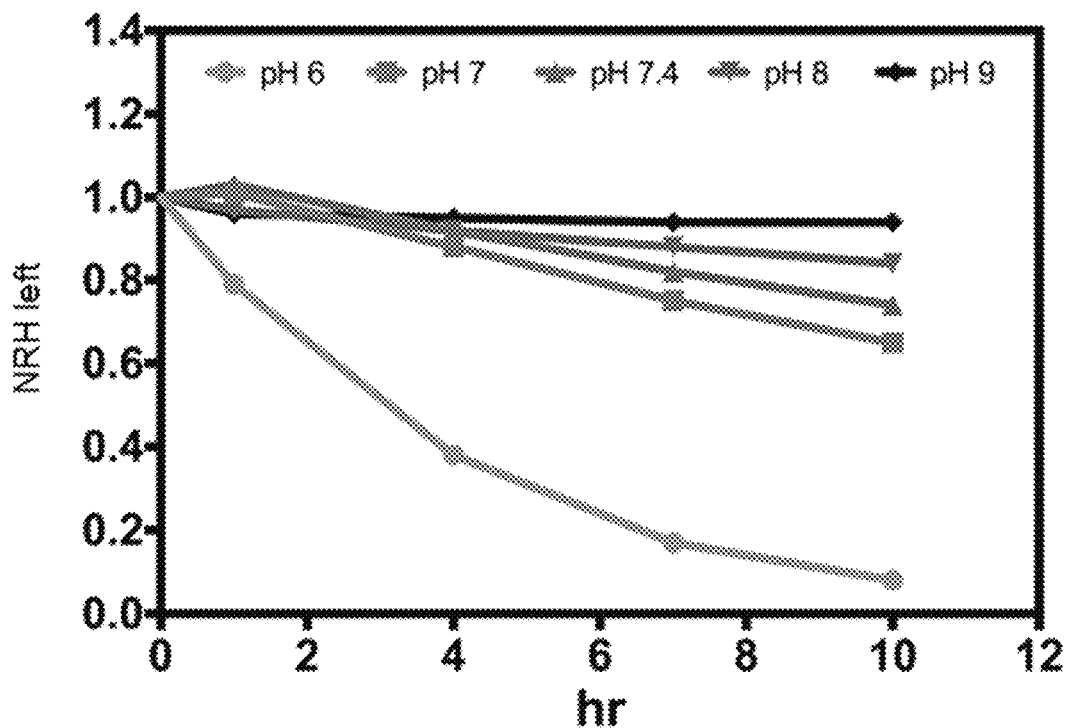
FIG. 10 shows the concentration over time of dihydronicotinamide riboside in aqueous solutions at pH values of 6, 7, 7.4, 8, and 9.

To further understand the chemical properties of NRH, NRH was incubated phosphate buffers pHed to 6, 7, 7.4, 8, and 9. HPLC chromatograph showed that NRH was rapidly degraded in slightly acidic buffer at pH 6. In a neutral pH, at pH 7 and pH 7.4, NRH was not very stable and degraded by 35% and 26% after 10 hr incubation at 10° C. NRH appears to be more stable at slightly alkaline conditions, in which 84% of NRH was remained at pH 8 and 94% of NRH was preserved at pH 9 after 10 hr as shown in FIG. 10. Therefore, NRH is more stable in slightly alkaline condition comparing to neutral or acidic environment.

Example 19

This example demonstrates that NRH protected cells from cytotoxicity by enhancing $NAD^+$ content.

Figure 11A:
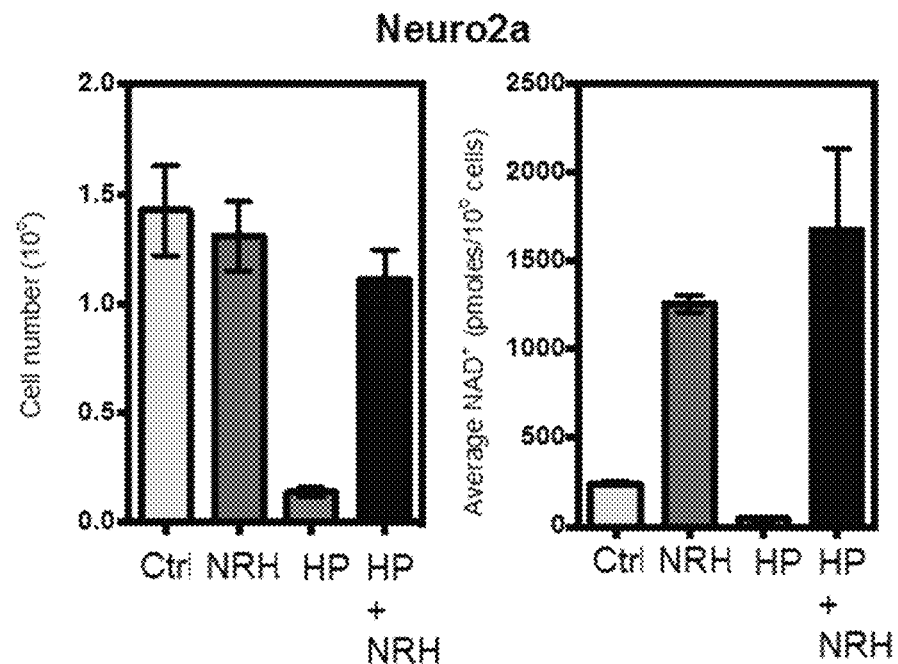
FIG. 11A shows the cell number and average NAD$^+$ concentration for Neuro2A cells treated with dihydronicotinamide riboside, hydrogen peroxide, or dihydronicotinamide riboside+hydrogen peroxide.
Figure 11B:
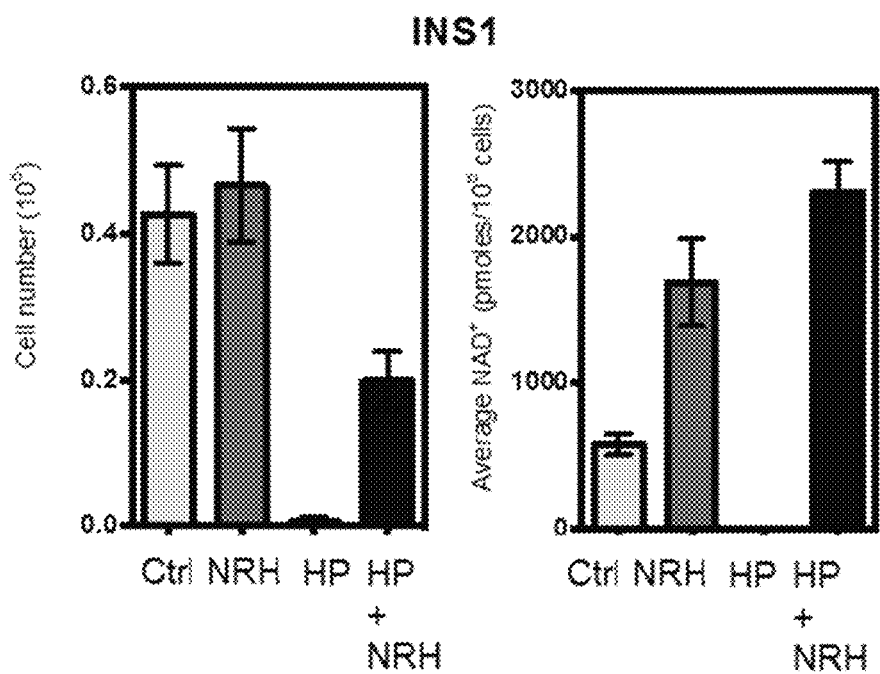
FIG. 11B shows the cell number and average NAD$^+$ concentration for INS1 cells treated with dihydronicotinamide riboside, hydrogen peroxide, or dihydronicotinamide riboside+hydrogen peroxide.
Figure 12A:
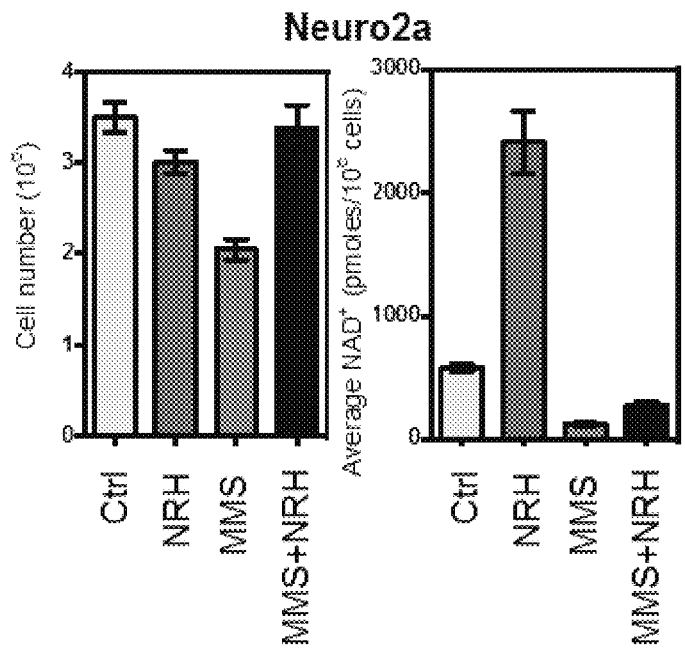
FIG. 12A shows the cell number and average NAD$^+$ concentration for Neuro2A cells treated with dihydronicotinamide riboside, methyl methanesulfonate (MMS), or dihydronicotinamide riboside+MMS.
Figure 12B:
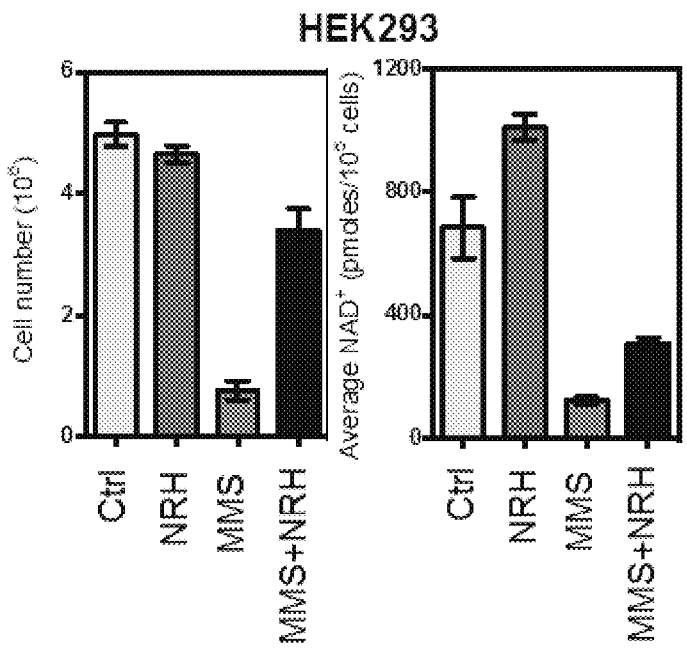
FIG. 12B shows the cell number and average NAD$^+$ concentration for HEK293 cells treated with dihydronicotinamide riboside, methyl methanesulfonate (MMS), or dihydronicotinamide riboside+MMS.
Figure 13:
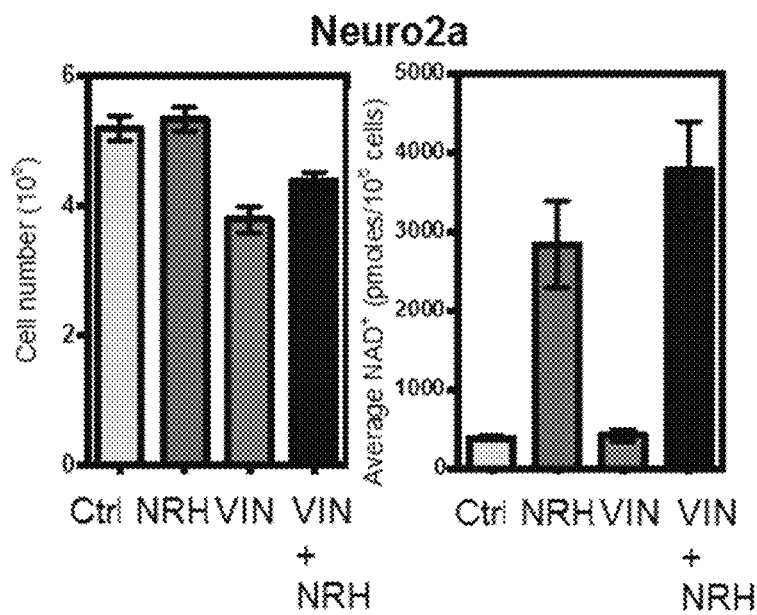
FIG. 13 shows the cell number and average NAD$^+$ concentration for HEK293 cells treated with dihydronicotinamide riboside, vincristine (VIN), or dihydronicotinamide riboside+VIN.

In order to evaluate if the $NAD^+$ enhancing effect of NRH can protect cells from oxidative stress and DNA damage-induced cytotoxicity, Neuro2a cells were treated with hydrogen peroxide or methyl methanesulfonate (MMS) with or without the presence of NRH. Both hydrogen peroxide and MMS induced significant cell death and $NAD^+$ depletion, but the addition of NRH preserved cellular $NAD^+$ content and protected the cells from cytotoxicity (FIG. 11A, FIG. 12A). Similar protection from NRH was also observed in INS1 cells (FIG. 11B) and HEK293 cells (FIG. 12B). Also, when stressed with a neurotoxin, vincristine, Neuro2a cells also suffered from cell death and $NAD^+$ deprivation, whereas NRH restored $NAD^+$ level in cells and maintained living cell count (FIG. 13).

Example 20

This example demonstrates that NRH preserved insulin-secretion capacity in beta cells.

Figure 14A:
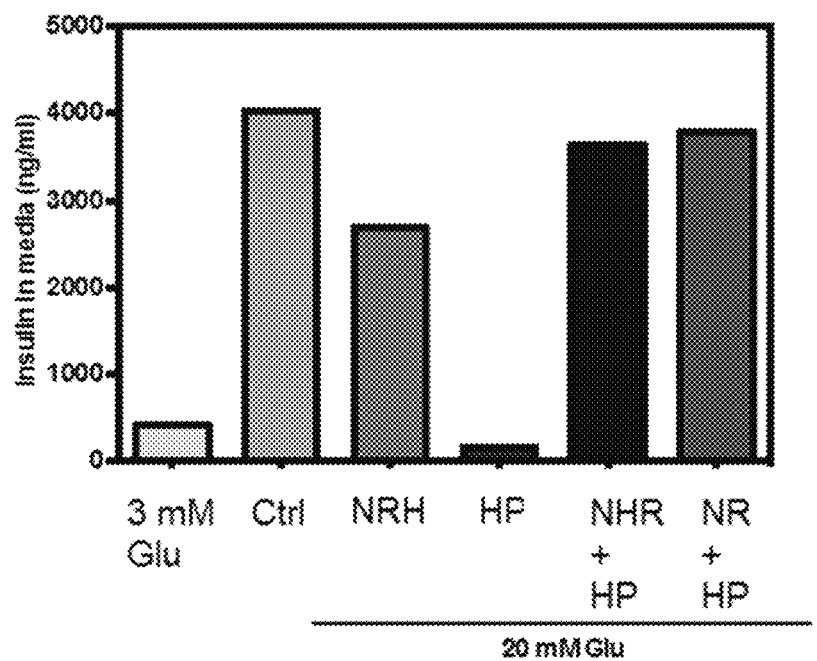
FIG. 14A shows the average NAD$^+$ concentration in INS1 cells treated with 3 mM glucose and with control, dihydronicotinamide riboside, hydrogen peroxide, dihydronicotinamide riboside+hydrogen peroxide, and nicotinamide riboside+hydrogen peroxide in the presence of 20 nM glucose.
Figure 14B:
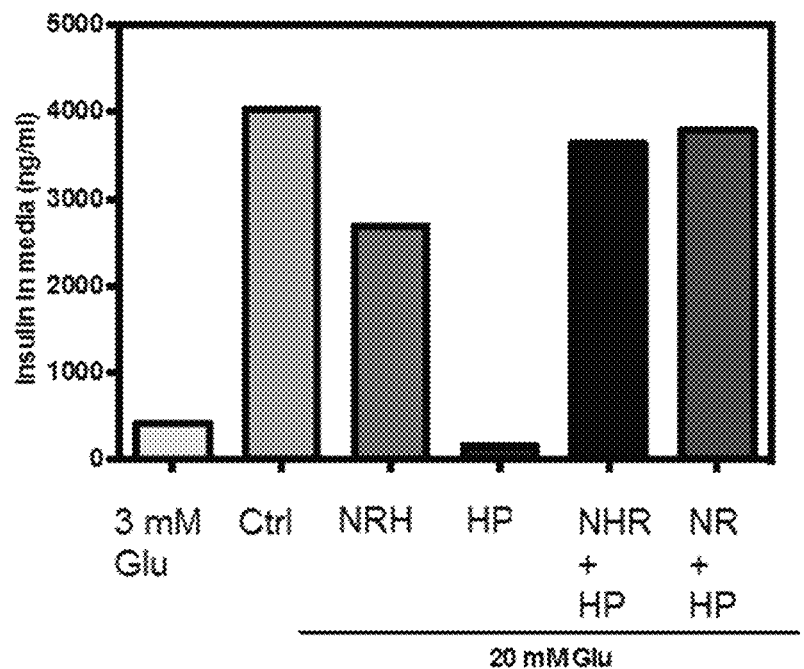
FIG. 14B shows the concentration of insulin in the media produced by INS1 cells treated with 3 mM glucose and with control, dihydronicotinamide riboside, hydrogen peroxide, dihydronicotinamide riboside+hydrogen peroxide, and nicotinamide riboside+hydrogen peroxide in the presence of 20 nM glucose.

To examine if NRH can preserve the normal insulin secreting function in beta cells under oxidative stress, hydrogen peroxide and NRH were added to INS1 cells in glucose-induced insulin secretion assay. NRH restored the $NAD^+$ level depleted by hydrogen peroxide treatment, even to a higher extent comparing to NR treatment as shown in FIG. 14A. When assessing the insulin secretion ability of INS1 cells, high glucose media induced a significantly increased insulin release into the media and the insulin secretion was largely sabotaged by hydrogen peroxide treatment. Addition of either NRH or NR has restored the insulin secretion level back to a similar extent as untreated control as shown in FIG. 14B, demonstrating both NRH and NR can protect the insulin secreting function of INS1 cells under oxidative stress induced by hydrogen peroxide.

Example 21

This example demonstrates that cellular $NAD^+$ concentration is increased in HEK cells by treatment with a dihydronicotinate riboside compound.

Figure 15:
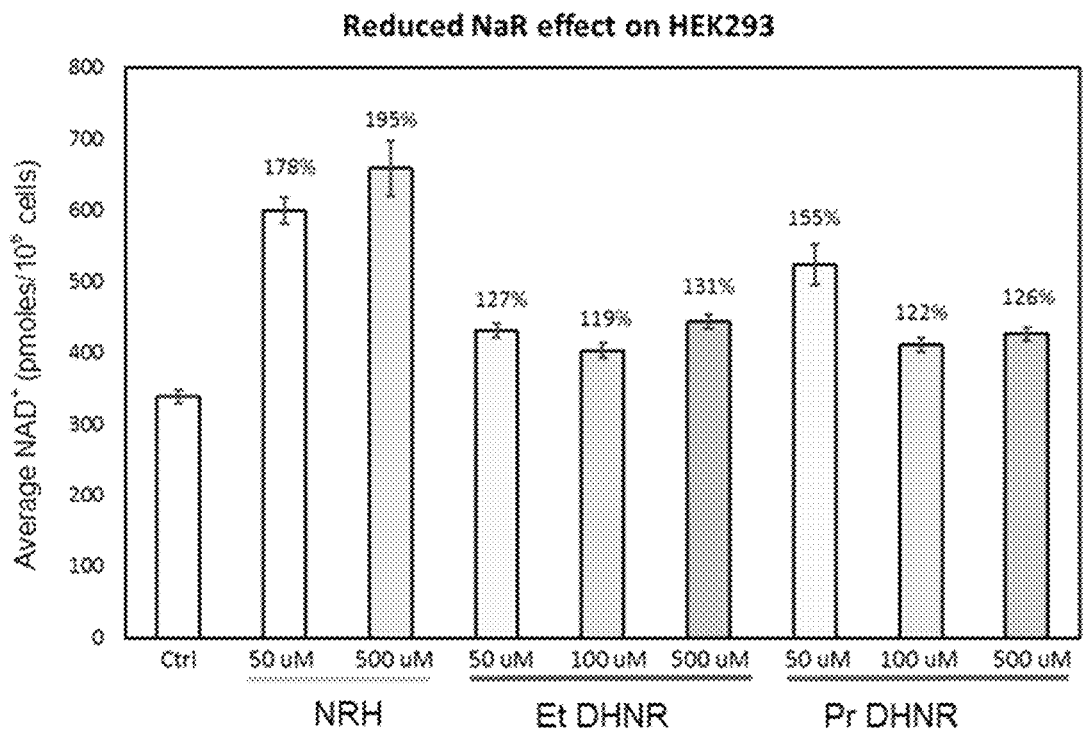
FIG. 15 shows the average NAD$^+$ concentration in HEK293 cells incubated for 6 h with the indicated concentrations of dihydronicotinamide riboside, 1,4-dihydro-ethyl nicotinate riboside, and 1,4-dihydro-propyl nicotinate riboside.

HEK cells were plated in 6-well plates until 90% confluent. Cells were treated with ethyl dihydronicotinate riboside (Et NaR-H, i.e. ethyl-1-((2R,3S,4R,5R)-3,4-dihydroxy-5-(hydroxymethyl)tetrahydrofuran-2-yl)-1,4-dihydropyridine- 3-carboxylate) (50 µM, 100 µM and 500 µM), propyl dihydronicotinate riboside (Pr NaR-H, i.e. propyl-1-((2R,3S,4R,5R)-3,4-dihydroxy-5-(hydroxymethyl)tetrahydrofuran-2-yl)-1,4-dihydropyridine-3-carboxylate) (50 µM, 100 µM and 500 µM), or dihydronicotinamide riboside (NHR) (50 µM and 500 µM) as a positive control. After 6 hours of incubation, cells were harvested with Trypsin. A cell count was obtained from each cell suspension by hemacytometer. The cell pellets were used for $NAD^+$ measurement. As shown in FIG. 15, cellular NAD concentration is increased by treatment with dihydronicotinate riboside compounds.

Example 22

This example demonstrates that cellular $NAD^+$ concentration is increased in HEK cells by treatment with a dihydronicotinate riboside compound.

HEK cells were plated in 6-well plates until 90% confluent. Cells were treated with butyl dihydronicotinate riboside (Bu NaR-H, i.e. butyl-1-((2R,3S,4R,5R)-3,4-dihydroxy-5-(hydroxymethyl)tetrahydrofuran-2-yl)-1,4-dihydropyridine-3-carboxylate) (50 µM), heptyl dihydronicotinate riboside (Hep NaR-H, i.e. heptyl-1-((2R,3S,4R,5R)-3,4-dihydroxy-5-(hydroxymethyl)tetrahydrofuran-2-yl)-1,4-dihydropyridine-3-carboxylate) (50 µM), octyl dihydronicotinate riboside (Oct NaR-H, i.e. octyl-1-((2R,3S,4R,5R)-3,4-dihydroxy-5-(hydroxymethyl)tetrahydrofuran-2-yl)-1,4-dihydropyridine-3-carboxylate) (50 µM) or dihydronicotinamide riboside (NHR) (50 µM) as a positive control. After 6 hours of incubation, cells were harvested with Trypsin. A cell count was obtained from each cell suspension by hemacytometer. The cell pellets were used for $NAD^+$ measurement. The average $NAD^+$ was determined and the percentages of average $NAD^+$ as compared to control are set forth in Table 2. As is apparent from the results set forth in Table 2, cellular NAD concentration is increased by treatment with dihydronicotinate riboside compounds.

TABLE 2

| Compound | Average $NAD^+$ (pmoles/$10^6$ cells) |
|---|---|
| NRH | 145% |
| Bu NaR—H | 124% |
| Hep NaR—H | 124% |
| Oct NaR—H | 112% |

Example 23

This example demonstrates the calculated octanol-water partition coefficients (c Log P) of compounds in accordance with an embodiment of the invention.

The octanol-water partition coefficients of compounds were calculated using the ChemDraw™ program version 12.0. The molecular weights and calculated c Log P values are set forth in Table 3.

TABLE 3

| X | MW | CLogP | MW | CLogP |
|---|---|---|---|---|
| $NH_2$ | 255 | −5.1 | 256 | −1.99 |
| OH | 256 | −4.19 | 257 | −1.25 |
| MeO | 270 | −4.42 | 271 | −0.73 |
| EtO | 284 | −3.89 | 285 | −0.20 |
| n-PrO | 298 | −3.37 | 299 | 0.33 |
| i-PrO | 298 | −3.59 | 299 | 0.11 |
| n-BuO | 312 | −2.84 | 313 | 0.86 |
| n-PeO | 326 | −2.31 | 327 | 1.38 |
| n-HexO | 340 | −1.78 | 341 | 1.91 |
| n-HepO | 354 | −1.25 | 355 | 2.44 |
| n-OctO | 368 | −0.72 | 369 | 2.97 |

As is apparent from the results set forth in Table 3, the dihydronicotinoyl riboside esters have octanol-water partition coefficients that are significantly higher than the octanol-water partition coefficients of the nicotinoyl riboside esters, indicating that the reduced compounds have significantly higher lipophilicity than the non-reduced compounds.

Example 24

This example demonstrates the effect of administration of NRH on NAD+ levels in whole blood in mice.

Figure 16:
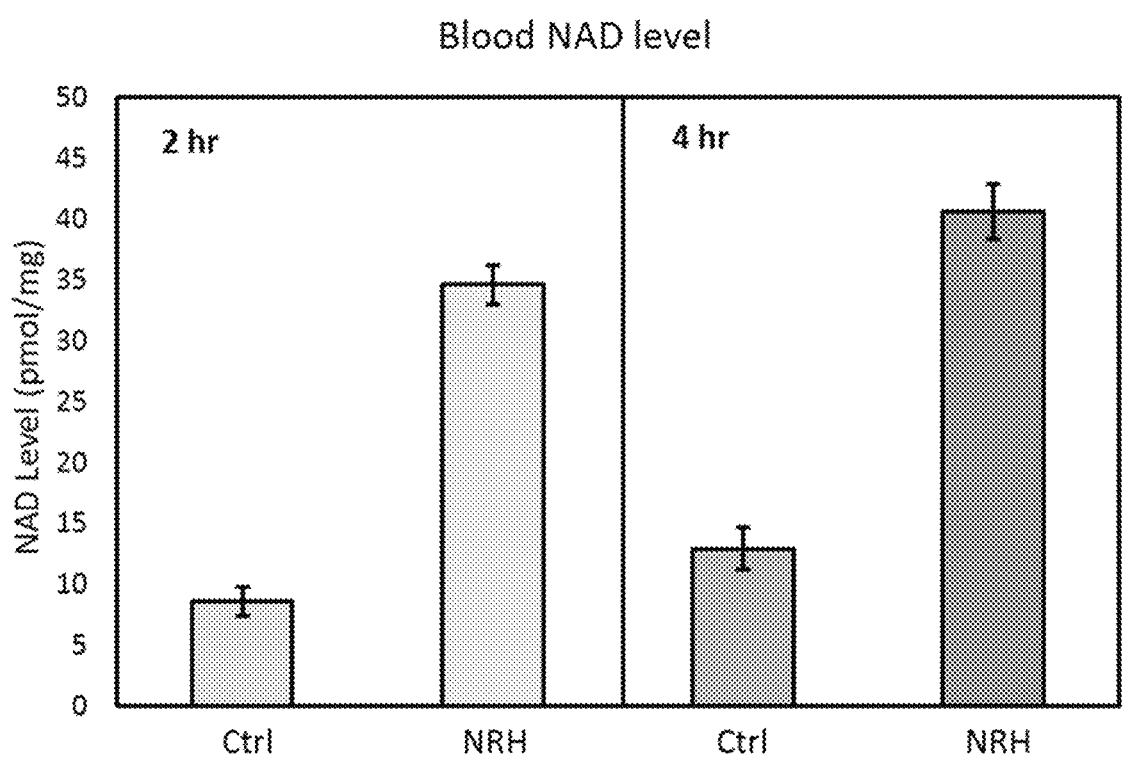
FIG. 16 shows blood levels of NAD+ in C57/B6 mice injected i.p. with 1000 mg/kg of dihydronicotinamide riboside at 2 h and 4 h after injection.

4 C57/B6 mice (mass ranges 25-30 g each) were injected intraperitoneally with 1000 mg/kg NRH with NRH dissolved in 100 microliter sterile phosphate buffered saline and 4 of the same littermates were injected the same volume of sterile phosphate buffered saline. At 2 and 4 hours blood was drawn by capillary and samples were assayed by known assay methods to assess for NAD content. The results are shown in FIG. 16. As is apparent from FIG. 16, NRH-treated animals have higher NAD levels at 2 and 4 hours in whole blood as compared with control animals injected at the same time with phosphate buffered saline.

Example 25

This example demonstrates the effect on $NAD^+$ levels in HEK293 cells resulting from treatment with dihydronicotinamide riboside (NRH) as compared to treatment with water and with nicotinamide riboside (NR).

HEK293 cells were treated with 1 mM NRH and with 1 mM NR as described in Example 11. $NAD^+$ cells were determined as compared to control and the results set forth in

TABLE 4

| Compound | Average $NAD^+$ (pmoles/$10^6$ cells) |
|---|---|
| NRH (1000 mM) | 236% |
| NR (1000 mM) | 148% |

As is apparent from the results set forth in Table 4, treatment of HEK293 cells with 1000 mM of NRH resulted in a 236% increase in NAD+, while treatment of HEL293 cells with 1000 mM of NR resulted in a 148% increase in NAD+.

The invention is exemplified by the following embodiments:

1. A compound of formula (I):

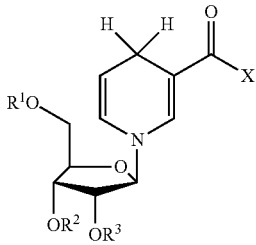

wherein $R^1$, $R^2$, and $R^3$ are independently selected from hydrogen, formyl, optionally substituted $C_1$-$C_{12}$ alkylcarbonyl, and $C_6$-$C_{10}$ optionally substituted arylcarbonyl, X is $NHR^4$, $NR^4R^5$, or $OR^6$, $R^4$ and $R^5$ are independently optionally substituted $C_1$-$C_{12}$ alkyl or optionally substituted $C_6$-$C_{10}$ aryl, and $R^6$ is hydrogen, optionally substituted $C_1$-$C_{12}$ alkyl, or optionally substituted $C_6$-$C_{10}$ aryl, wherein the alkyl or aryl portion of $R^4$-$R^6$ is optionally substituted with one or more substituents selected from halo, amino, alkyl, alkoxy, aryloxy, hydroxyalkyl, and any combination thereof, with the provisos that, when X is $OR^6$ and $R^6$ is hydrogen, $R^1$, $R^2$, and $R^3$ are not all hydrogen or acetyl, when X is $OR^6$ and $R^6$ is hydrogen, $R^1$ is not benzoyl and $R^2$ and $R^3$ are not hydrogen, and when X is $OR^6$ and $R^6$ is methyl or ethyl, $R^1$, $R^2$, and $R^3$ are not all acetyl, or a salt thereof.

2. The compound of embodiment 1, wherein X is $OR^6$, $R^6$ is optionally substituted $C_1$-$C_{12}$ alkyl, and $R^1$, $R^2$, and $R^3$ are hydrogen.

3. The compound of embodiment 1 or 2, wherein the compound is selected from:

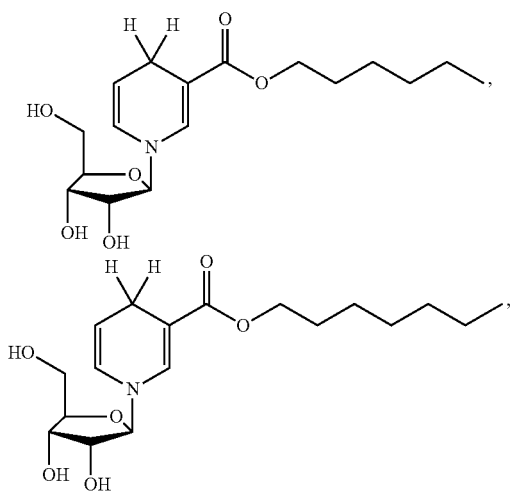

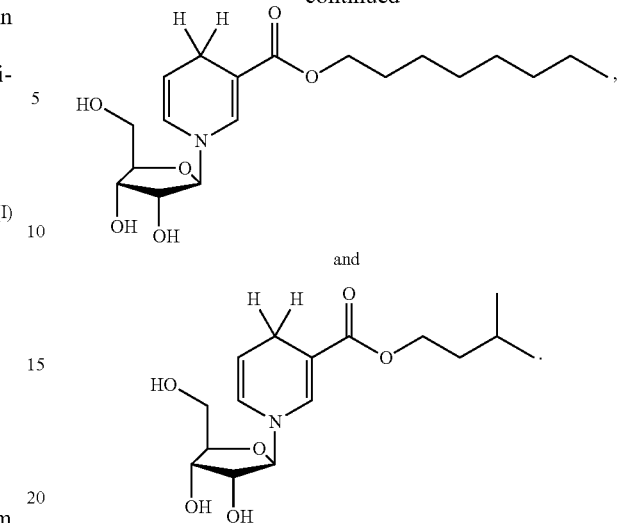

4. The compound of embodiment 1, wherein X is $OR^6$, $R^6$ is optionally substituted $C_1$-$C_{12}$ alkyl, and $R^1$, $R^2$, and $R^3$ are $C_1$-$C_{12}$ alkylcarbonyl.

5. The compound of embodiment 1, wherein X is $NHR^4$.

6. The compound of embodiment 1, wherein X is $NR^4R^5$.

7. The compound of embodiment 5 or 6, wherein $R^1$, $R^2$, and $R^3$ are hydrogen.

8. The compound of embodiment 5 or 6, wherein $R^1$, $R^2$, and $R^3$ are $C_1$-$C_{12}$ alkylcarbonyl.

9. A pharmaceutical composition comprising a compound of any one of embodiments 1-8 or a pharmaceutically acceptable salt thereof, and a pharmaceutically acceptable carrier.

10. A dietary supplement or food ingredient composition comprising a compound of any one of embodiments 1-8 or a salt thereof.

11. A process for the preparation of a compound of formula (II):

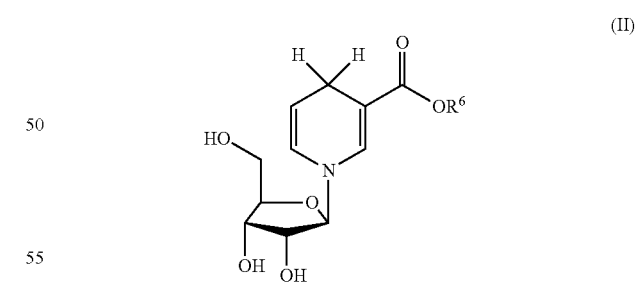

wherein $R^1$, $R^2$, and $R^3$ are independently selected from hydrogen, formyl, optionally substituted $C_1$-$C_{12}$ alkylcarbonyl, and $C_6$-$C_{10}$ optionally substituted arylcarbonyl, and $R^6$ is hydrogen, optionally substituted $C_1$-$C_{12}$ alkyl, or optionally substituted $C_6$-$C_{10}$ aryl, wherein the alkyl or aryl portion of $R^6$ is optionally substituted with one or more substituents selected from halo, amino, alkyl, alkoxy, aryloxy, hydroxyalkyl, and any combination thereof, wherein the process comprises the steps of:
(i) providing a compound of formula (III):

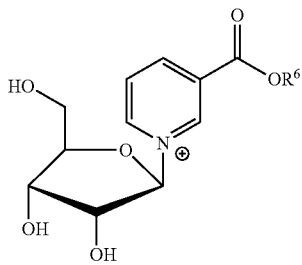

(ii) reducing the compound of formula (III) with a reducing agent to provide the compound of formula (II), and
(iii) isolating the compound of formula (II).

12. The process of embodiment 11, wherein the reducing agent is sodium dithionate.

13. The process of embodiment 11, wherein the compound of formula (III) is isolated by chromatography.

14. A method for increasing cell NAD$^+$ production comprising administering to a cell a compound of any one of embodiments 1-8 or a salt thereof.

15. The method of embodiment 14, wherein the cell is in a mammal having a lipid disorder, a metabolic dysfunction, a cardiovascular disease, CNS or PNS trauma, a neurodegenerative disease or condition, or hearing loss, or is in a mammal that has been exposed to a toxic agent.

16. The method of embodiment 14, wherein the cell is in a mammal at risk for hearing loss.

17. The method of embodiment 14, wherein the cell is in a mammal, wherein the compound is administered in an amount effective for promoting the function of the metabolic system, promoting muscle function or recovery, promoting the function of the auditory system, or promoting cognitive function.

18. A method of improving mitochondrial densities in a cell, wherein the method comprises administering to the cell a compound of any one of embodiments 1-8 or a salt thereof.

19. The method of embodiment 18, wherein the cell is in a mammal having a lipid disorder, a metabolic dysfunction, a cardiovascular disease, CNS or PNS trauma, a neurodegenerative disease or condition, hearing loss, or is in a mammal that has been exposed to a toxic agent.

20. The method of embodiment 18, wherein the cell is in a mammal at risk for hearing loss.

21. The method of embodiment 18, wherein the cell is in a mammal, wherein the compound is administered in an amount effective for promoting the function of the metabolic system, promoting muscle function or recovery, promoting the function of the auditory system, or promoting cognitive function.

22. A method for increasing mammalian cell and tissue NAD$^+$ production comprising administering to a cell a compound of any one of claims 1-8 or a salt thereof.

23. The method of embodiment 22, wherein the disease or condition results from toxic effects of high fat diets.

24. A method of treating or preventing a disease or condition in a mammal in need thereof, wherein the method comprises administering to the mammal a compound of any one of embodiments 1-8 or a salt thereof, wherein the disease or condition is neurodegeneration caused by Alzheimer's disease.

25. A method of improving mitochondrial densities, insulin sensitivity, or exercise endurance in a mammal, wherein the method comprises administering to the mammal a compound of any one of embodiments 1-8 or a salt thereof.

26. A method of protecting a mammal from neurotrauma, wherein the method comprises administering to the mammal a compound of any one of embodiments 1-8 or a salt thereof.

27. The method of embodiment 26, wherein neurotrauma results from blast injury or noise.

27. A method of reducing toxicity induced by a HMGCoA reductase inhibitor in a mammal, which method comprises administering to the mammal a therapeutically effective amount of a compound of any one of embodiments 1-8 or a salt thereof,
wherein the mammal has been administered the HMG-CoA reductase inhibitor in an amount that produces toxicity in the mammal in the absence of the administration of the compound of formula (I), and
wherein the administration of the compound of embodiment 1 reduces the toxicity in the mammal.

28. A method of reducing toxicity induced by a HMGCoA reductase inhibitor in a mammal, which method comprises administering to the mammal a therapeutically effective amount of a compound of any one of embodiments 1-8 or a salt thereof and then administering to the mammal the HMGCoA reductase inhibitor in an amount that produces toxicity in the mammal in the absence of the administration of the compound of formula (I), whereby toxicity that would have been induced by the HMGCoA reductase inhibitor is reduced in the mammal by the administration of the compound of any one of claims 1-8.

29. A method of reducing toxicity induced by a HMGCoA reductase inhibitor in a mammal, which method comprises administering to the mammal a therapeutically effective amount of a compound of any one of embodiments 1-8 or a salt thereof, whereby toxicity induced by the HMGCoA inhibitor is reduced in the mammal, wherein the compound of formula (I) is administered to the mammal following manifestation of toxicity by the mammal.

30. A method of reducing toxicity induced by a genotoxic agent in a mammal, which method comprises administering to the mammal a therapeutically effective amount of a compound of any one of embodiments 1-8 or a salt thereof, wherein the mammal has been administered the genotoxic agent in an amount that produces toxicity in the mammal in the absence of the administration of the compound of formula (I), and wherein the administration of the compound reduces the toxicity in the mammal.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method for increasing cell $NAD^+$ production or for improving mitochondrial densities in a cell consisting of administering to a cell a compound of formula (I):

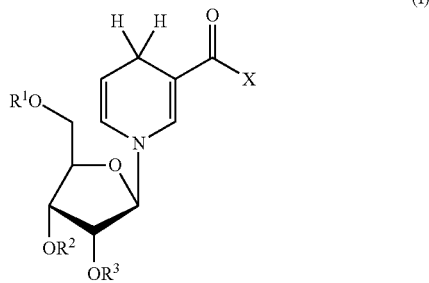

wherein $R^1$, $R^2$, and $R^3$ are each hydrogen, and X is $NH_2$, or a salt thereof,
optionally in combination with a multi-vitamin, a mineral, an acceptable carrier, or any combination thereof.

2. The method of claim 1, wherein the method increases cell NAD+ production.

3. The method of claim 2, wherein the cell is in a mammal having a lipid disorder, a metabolic dysfunction, a cardiovascular disease, CNS or PNS trauma, a neurodegenerative disease or condition, or hearing loss, or is in a mammal that has been exposed to a toxic agent.

4. The method of claim 2, wherein the cell is in a mammal that has hearing loss.

5. The method of claim 2, wherein the cell is in a mammal, wherein the compound is administered in an amount effective for promoting the function of the metabolic system, promoting muscle function or recovery, promoting the function of the auditory system, or promoting cognitive function.

6. The method of claim 1, wherein the method improves mitochondrial densities in the cell.

7. The method of claim 6, wherein the cell is in a mammal having a lipid disorder, a metabolic dysfunction, a cardiovascular disease, CNS or PNS trauma, a neurodegenerative disease or condition, hearing loss, or is in a mammal that has been exposed to a toxic agent.

8. The method of claim 6, wherein the cell is in a mammal that has hearing loss.

9. The method of claim 6, wherein the cell is in a mammal, wherein the compound is administered in an amount effective for promoting the function of the metabolic system, promoting muscle function or recovery, promoting the function of the auditory system, or promoting cognitive function.

10. A dietary supplement or food ingredient composition comprising the compound of claim 1 or a salt thereof, wherein the dietary supplement or food ingredient composition is a solid composition suitable for oral administration comprising the compound or salt and an acceptable carrier.

11. A method for increasing $NAD^+$ concentration in a mammal consisting of administering to the mammal a compound of formula (I):

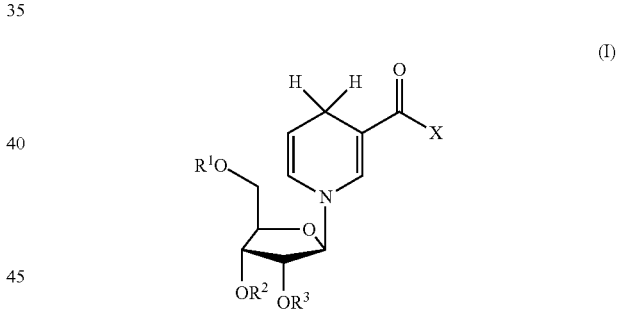

wherein $R^1$, $R^2$, and $R^3$ are each hydrogen, and X is $NH_2$, or a salt thereof, optionally in combination with a multi-vitamin, a mineral, an acceptable carrier, or any combination thereof.

12. The method of claim 11, wherein the administration increases $NAD^+$ concentration in blood of the mammal.

13. The method of claim 11, wherein the administration increases $NAD^+$ concentration in a tissue of the mammal.

* * * * *